US008207199B2

(12) United States Patent
Aoki et al.

(10) Patent No.: US 8,207,199 B2
(45) Date of Patent: Jun. 26, 2012

(54) AZOLE COMPOUND

(75) Inventors: Satoshi Aoki, Tokyo (JP); Ryosuke Munakata, Tokyo (JP); Noriyuki Kawano, Tokyo (JP); Kiyohiro Samizu, Tokyo (JP); Hiromasa Oka, Tokyo (JP); Takahiro Ishii, Tokyo (JP); Takashi Sugane, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/054,057

(22) PCT Filed: Jul. 13, 2009

(86) PCT No.: PCT/JP2009/062680
§ 371 (c)(1),
(2), (4) Date: Jan. 13, 2011

(87) PCT Pub. No.: WO2010/007966
PCT Pub. Date: Jan. 21, 2010

(65) Prior Publication Data
US 2011/0118311 A1 May 19, 2011

(30) Foreign Application Priority Data

Jul. 14, 2008 (JP) ................ P2008-182251

(51) Int. Cl.
*A61K 31/4545* (2006.01)
*C07D 417/14* (2006.01)
*C07D 401/14* (2006.01)
*C07D 413/14* (2006.01)

(52) U.S. Cl. ........................................ 514/318; 546/194
(58) Field of Classification Search .................. 514/318; 546/194
See application file for complete search history.

(56) References Cited

U.S. PATENT DOCUMENTS

| 2007/0021405 A1 | 1/2007 | Abouabdellah et al. |
| 2008/0306046 A1 | 12/2008 | Ishii et al. |
| 2008/0312226 A1 | 12/2008 | Matsumoto et al. |
| 2009/0048263 A1 | 2/2009 | Matsumoto et al. |
| 2010/0009971 A1 | 1/2010 | Ishii et al. |
| 2010/0009972 A1 | 1/2010 | Ishii et al. |

FOREIGN PATENT DOCUMENTS

| JP | 2007-524707 | 8/2007 |
| WO | WO-03/051841 A2 | 6/2003 |
| WO | WO-03/065989 A2 | 8/2003 |
| WO | WO-2004/033422 A2 | 4/2004 |
| WO | WO-2005/044797 A1 | 5/2005 |
| WO | WO 2005/090347 A1 | 9/2005 |
| WO | WO-2005/090347 A1 | 9/2005 |
| WO | WO-2006/054652 A1 | 5/2006 |
| WO | WO-2006/088075 A1 | 8/2006 |
| WO | WO-2006/129199 A1 | 12/2006 |
| WO | WO-2007/005510 A1 | 1/2007 |
| WO | WO-2007/020888 A1 | 2/2007 |

OTHER PUBLICATIONS

McKinney et al., "Structure and Function of Fatty Acid Amide Hydrolase," Annual Review of Biochemistry, vol. 74, pp. 411-432, (2005).
Pertwee, "Pharmacology of Cannabinoid Receptor Ligands," Current Medicinal Chemistry, vol. 6, pp. 635-664, (1999).
Barnes, "Sativex®: Clinical Efficacy and Tolerability in the Treatment of Symptoms of Multiple Sclerosis and Neuropathic Pain," Expert Opinion of Pharmacotherapy, vol. 7, pp. 607-615, (2006).
Jhaveri et al., "Endocannabinoid Metabolism and Uptake: Novel Targets for Neuropathic and Inflammatory Pain," British Journal of Pharmacology, vol. 152, pp. 624-632, (2007).
Kathuria et al., "Modulation of Anxiety Through Blockade of Anandamide Hydrolysis," Nature Medicine, vol. 9, No. 1, pp. 76-81, (2003).
Seierstad et al., "Discovery and Development of Fatty Acid Amide Hydrolase (FAAH) Inhibitors," Journal of Medicinal Chemistry, vol. 51, No. 23, pp. 7327-7343, (2008).
International Search report from the Japanese Patent Office for International Application No. PCT/JP2009/062680, (Mail Date: Sep. 2, 2009).
Supplementary European Search Report from the European Patent Office in corresponding European Application No. 09797891.0, dated Jun. 28, 2011.

*Primary Examiner* — Raymond Henley, III
(74) *Attorney, Agent, or Firm* — Finnegan, Henderson, Farabow, Garrett & Dunner, L.L.P.

(57) ABSTRACT

A compound which is useful as an active ingredient of a pharmaceutical composition for treating neuropathic pain is provided. The present inventors have made extensive studies on compounds having an FAAH inhibitory activity, and as a result, have found that an azole compound substituted with an N-(pyridine-3-yl)oxycarbonyl-piperidin-4-yl group and a phenyl group or a pharmaceutically acceptable salt thereof has an excellent FAAH inhibitory activity, thereby completing the present invention. The compound of the present invention is confirmed to have an excellent FAAH inhibitory activity and an antiallodynic effect in rat models with neuropathic pain, and thus is useful as an agent for preventing and/or an agent for treating neuropathic pain.

12 Claims, No Drawings

AZOLE COMPOUND

TECHNICAL FIELD

The present invention relates to an azole compound which is useful as an active ingredient of a pharmaceutical composition, particularly a pharmaceutical composition for treating neuropathic pain.

BACKGROUND ART

Fatty acid amide hydrolase (FAAH) is known to hydrolyze endocannabinoid to inactivate it (Non-Patent Document 1). Endocannabinoid is a generic term for biomolecules that act on cannabinoid receptors to exhibit their physiological activities. As typical endocannabinoids, anandamide, palmitoylethanolamide, oleamide, and 2-arachidonoylglycerol are known. Furthermore, Δ9-tetrahydrocannabinol which is considered as an active ingredient of Cannabis (marijuana) is known to activate a cannabinoid receptor (Non-Patent Document 2).

In mammals, two types of cannabinoid receptors, CB1 and CB2, have heretofore been known. CB1 is expressed in the central and peripheral nervous systems, and when activated, it exhibits a psychological action, an analgesic action, or the like. CB2 is expressed in the immune system, and when activated, it exhibits an anti-inflammatory action, an analgesic (inflammatory) action, or the like.

Nonsteroidal anti-inflammatory drugs, and narcotic analgesic drugs such as morphine and the like, that are ordinary analgesics, are known to be weakly effective for neuropathic pain. In the medical field, antiepileptic drugs such as pregabalin and the like, and antidepressant drugs such as duloxetine and the like are used for pain relief, but their analgesic effects are insufficient, and there are problems with central side effects such as sleepiness, dizziness, and the like.

A cannabinoid receptor agonist exhibits effectiveness for patients with neuropathic pain, but its use is greatly limited due to its psychological action (Non-Patent Document 3).

On the other hand, when an FAAH inhibitor is administered to an animal, it exhibits an analgesic effect against neuropathic pain and inflammatory pain, but side effects observed when a cannabinoid receptor agonist is administered to an animal, such as sedation, decreased body temperature, catalepsy, and the like, are not observed (Non-Patent Documents 4 and 5), and thus an FAAH inhibitor is expected to be an excellent pharmaceutical for treating pain, in particular, a pharmaceutical for treating neuropathic pain.

As compounds having an FAAH inhibitory activity, compounds which are capable of acting as an analgesic, an antianxiety drug, an antiepileptic drug, an antidepressant, an antiemetic, a cardiovascular agent, or an antiglaucomatous agent, are known.

For example, Patent Document 1 discloses the compound represented by the following formula (A), as a compound having an FAAH inhibitory activity.

[Chem. 1]

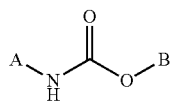

(A)

(In the formula, B represents a variety of ring groups which may be substituted, or the like, and A represents phenyl which may be substituted, phenylalkyl which may be substituted, dibenzofuranyl, dibenzothienyl, naphthoyl, indolyl, fluorenyl, or carbazolyl. For the details, refer to this publication).

Furthermore, Patent Document 2 discloses the compound represented by the following formula (B) as a compound having an FAAH inhibitory activity.

[Chem. 2]

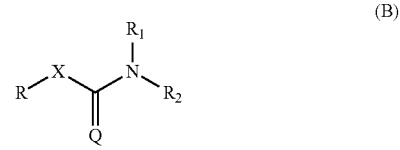

(B)

(In the formula, R represents a variety of ring groups which may be substituted, or the like, and X and Q are the same as or different from each other and represent O or S, respectively. Further, $R_1$ and $R_2$ may be combined with an N atom to which they optionally bind to form a substituted or unsubstituted ring. For the details, refer to this publication).

Furthermore, Patent Document 3 discloses the compound represented by the following formula (C) as a compound having an FAAH inhibitory activity.

[Chem. 3]

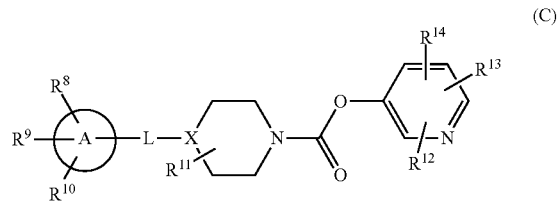

(C)

(For the details, refer to this publication).

All of the compounds disclosed in this document have different structures from the compound of the formula (I) of the present invention.

Furthermore, Patent Documents 4 and 5 disclose the urea compound represented by the following formula (D) as an FAAH inhibitor.

[Chem. 4]

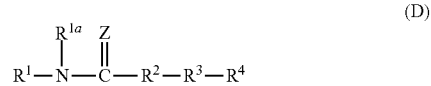

(D)

(In the formula, Z represents O or S, and $R^2$ represent piperidine-1,4-diyl or piperazine-1,4-diyl, each of which may be substituted. For the details, refer to these publications).

LIST OF THE DOCUMENTS

Patent Documents

[Patent Document 1] Pamphlet of International Publication No. WO2003/065989

[Patent Document 2] Pamphlet of International Publication No. WO2004/033422

[Patent Document 3] Pamphlet of International Publication No. WO2006/088075
[Patent Document 4] Pamphlet of International Publication No. WO2006/054652
[Patent Document 5] Pamphlet of International Publication No. WO2007/020888
Non-Patent Documents
[Non-Patent Document 1] "Annual review of biochemistry", (USA), 2005, Vol. 74, p. 411-432
[Non-Patent Document 2] "Current Medicinal Chemistry", (USA), 1999, Vol. 6, p. 635-664
[Non-Patent Document 3] "Expert opinion on pharmacotherapy", (UK), 2006, Vol. 7, p. 607-615
[Non-Patent Document 4] "British Journal of Pharmacology", (UK), 2007, Vol. 152, p. 624-32
[Non-Patent Document 5] "Nature Medicine", (UK), 2003, Vol. 9, p. 76-81

SUMMARY OF THE INVENTION

Problem that the Invention is to Solve

A compound which is useful as an active ingredient of a pharmaceutical composition, in particular, a pharmaceutical composition for treating pain in which there is no or a reduced concern about side effects and addictiveness like those of Cannabis, is provided.

Means for Solving the Problem

The present inventors made extensive studies on compounds having an FAAH inhibitory activity, and as a result, found that a compound of the formula (I) exhibits an excellent FAAH inhibitory activity, thereby completing the present invention.
That is, the present invention relates to the compound of the formula (I) or a pharmaceutically acceptable salt thereof, and a pharmaceutical composition containing the compound of the formula (I) or a pharmaceutically acceptable salt thereof, and a pharmaceutically acceptable excipient.

[Chem. 5]

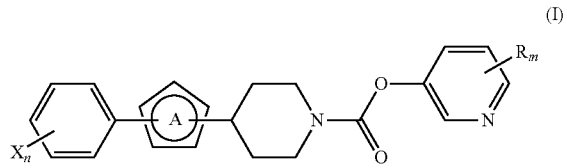

(I)

(wherein
Ring A represents an azole ring,
R is the same as or different from each other, and represents H or lower alkyl,
X is the same as or different from each other, and represents H, halogen, or halogeno-lower alkyl,
n and m are the same as or different from each other and represent 1 or 2).

In addition, the present invention relates to a pharmaceutical composition for treating neuropathic pain containing the compound of the formula (I) or a pharmaceutically acceptable salt thereof, that is, an agent for treating neuropathic pain containing the compound of the formula (I) or a pharmaceutically acceptable salt thereof.

Further, the present invention relates to use of the compound of the formula (I) or a pharmaceutically acceptable salt thereof for the manufacture of a pharmaceutical composition for treating neuropathic pain, and a method for treating neuropathic pain, comprising administering to a patient an effective amount of the compound of the formula (I) or a pharmaceutically acceptable salt thereof.

Effects of the Invention

The compound of the formula (I) or a pharmaceutically acceptable salt thereof has an FAAH inhibitory activity, and can be used as an agent for preventing and/or treating FAAH-related diseases, in particular, neuropathic pain.

BEST MODE FOR CARRYING OUT THE INVENTION

Hereinbelow, the present invention will be described in detail.
The "lower alkyl" is a linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl group, or the like. In another embodiment, it is $C_{1-4}$ alkyl, in a further embodiment, methyl or ethyl, and in a further embodiment, methyl.
The "azole ring" means a ring having 2 to 4 hetero atoms selected from O, S, and N as atoms constituting the ring in which at least one of the hetero atoms is N, among the monocyclic conjugated unsaturated 5-membered rings. According to the arrangement of the hetero atoms in the ring, examples thereof include 1,2-azole, 1,3-azole, 1,2,4-azole, 1,2,3,4-azole, and the like, examples of 1,2-azole include pyrazole, isoxazole, and isothiazole, examples of the 1,3-azole include imidazole, oxazole, and thiazole, examples of the 1,2,4-azole include 1,2,4-triazole, 1,2,4-oxadiazole, 1,2,4-thiadiazole, and 1,2,4-oxathiazole, and examples of the 1,2,3,4-azole include tetrazole and the like. When the "azole ring" is a divalent ring group, it represents a divalent group formed by the removal of a hydrogen atom at any position.
The "halogen" means F, Cl, Br, or I.
The "halogeno-lower alkyl" means a linear or branched alkyl having 1 to 6 carbon atoms ($C_{1-6}$ alkyl) substituted with 1 to 5 halogens.
The "neuropathic pain" means pain caused by peripheral or central nervous system dysfunction, and examples thereof include diabetic neuropathic pain, postherpetic pain, HIV-induced neuropathy, an anticancer agent-induced neuropathy, post-spinal cord injury pain, or pain accompanying multiple sclerosis, and the like. The main clinical symptoms for the neuropathic pain include gripping pain, burning pain, hyperalgesia, allodynia, and the like.
Embodiments regarding the compound of the formula (I) will be presented below.
(1) The compound, in which Ring A is 1,2-azole, 1,3-azole, 1,2,4-azole, or 1,3,4-azole, in another embodiment, Ring A is 1,2,4-oxadiazole, 1,2,4-triazole, 1,3-oxazole, or pyrazole, or in a further embodiment, Ring A is one of the rings represented by the following formulae (II) to (VI):

[Chem. 6]

(II)

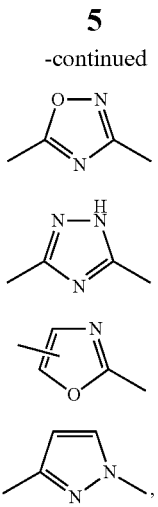

in a further embodiment, Ring A is one of the rings represented by the formulae (IV) to (VI). In a further embodiment, the compound in which Ring A is a ring represented by the formula (IV). In a further embodiment, the compound in which Ring A is a ring represented by the formula (V). In a further embodiment, the compound in which Ring A is a ring represented by the formula (VI).

(2) The compound, in which $R_m$ is H, 2-methyl, 6-methyl, or 2,6-dimethyl, and in another embodiment, $R_m$ is H, 2-methyl, or 6-methyl.

(3) The compound, in which $X_n$ is H, 2-fluoro, 3-fluoro, 4-fluoro, or 3,4-difluoro.

(4) The compound, which is a combination of two or more of the groups as described in (1) to (3) above.

Examples of the specific compound encompassed by the present invention include the compounds presented in (5) or (6) below, or pharmaceutically acceptable salts thereof:

(5) pyridin-3-yl 4-[3-(4-fluorophenyl)-1,2,4-oxadiazol-5-yl]piperidine-1-carboxylate,
pyridin-3-yl 4-(3-phenyl-1H-1,2,4-triazol-5-yl)piperidine-1-carboxylate,
6-methylpyridin-3-yl 4-[3-(4-fluorophenyl)-1H-1,2,4-triazol-5-yl]piperidine-1-carboxylate,
6-methylpyridin-3-yl 4-[5-(4-fluorophenyl)-1,3-oxazol-2-yl]piperidine-1-carboxylate,
2-methylpyridin-3-yl 4-[5-(4-fluorophenyl)-1,3-oxazol-2-yl]piperidine-1-carboxylate,
2,6-dimethylpyridin-3-yl 4-[5-(3,4-difluorophenyl)-1,2,4-oxadiazol-3-yl]piperidine-1-carboxylate,
2-methylpyridin-3-yl 4-[3-(2-fluorophenyl)-1H-1,2,4-triazol-5-yl]piperidine-1-carboxylate,
6-methylpyridin-3-yl 4-(3-phenyl-1H-pyrazol-1-yl)piperidine-1-carboxylate,
2-methylpyridin-3-yl 4-[5-(3-fluorophenyl)-1,3-oxazol-2-yl]piperidine-1-carboxylate, and
6-methylpyridin-3-yl 4-[4-(4-fluorophenyl)-1,3-oxazol-2-yl]piperidine-1-carboxylate.

(6) pyridin-3-yl 4-(3-phenyl-1H-1,2,4-triazol-5-yl)piperidine-1-carboxylate,
6-methylpyridin-3-yl 4-[3-(4-fluorophenyl)-1H-1,2,4-triazol-5-yl]piperidine-1-carboxylate,
6-methylpyridin-3-yl 4-[5-(4-fluorophenyl)-1,3-oxazol-2-yl]piperidine-1-carboxylate,
2,6-dimethylpyridin-3-yl 4-[5-(3,4-difluorophenyl)-1,2,4-oxadiazol-3-yl]piperidine-1-carboxylate,
2-methylpyridin-3-yl 4-[3-(2-fluorophenyl)-1H-1,2,4-triazol-5-yl]piperidine-1-carboxylate,
6-methylpyridin-3-yl 4-(3-phenyl-1H-pyrazol-1-yl)piperidine-1-carboxylate,
2-methylpyridin-3-yl 4-[5-(3-fluorophenyl)-1,3-oxazol-2-yl]piperidine-1-carboxylate, and
6-methylpyridin-3-yl 4-[4-(4-fluorophenyl)-1,3-oxazol-2-yl]piperidine-1-carboxylate.

The compound of the formula (I) may have tautomers or geometrical isomers in some cases, depending on the kind of substituents. In the present specification, the compound of the formula (I) shall be described in only one form of the isomers, yet the present invention includes other isomers, isolated forms of the isomers, or a mixture thereof.

In addition, the compound of the formula (I) may have asymmetric carbon atom(s) or axial asymmetry in some cases, and correspondingly, it may exist in the form of optical isomers. The present invention includes both an isolated form of these optical isomers of the compound of the formula (I) or a mixture thereof.

In addition, the pharmaceutically acceptable prodrugs of the compound represented by the formula (I) are also included in the present invention. The pharmaceutically acceptable prodrug refers to a compound having a group which can be converted into amino group, hydroxyl group, carboxyl group, or the like, by solvolysis or under a physiological condition. Examples of the group for forming a prodrug include those as described in Prog. Med., 5, 2157-2161 (1985) or "*Iyakuhin no Kaihatsu* (Pharmaceutical Research and Development)" (Hirokawa Publishing Company, 1990), vol. 7, *Bunshi Sekkei* (Drug Design), 163-198.

Furthermore, the compound of the formula (I) may form an acid addition salt or a salt with a base, depending on the kind of sub stituents, and these salts are included in the present invention as long as they are pharmaceutically acceptable salts. Specifically, examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or salts with organic bases such as methylamine, ethylamine, ethanolamine, lysine, ornithine, and the like, salts with various amino acids and amino acid derivatives such as acetylleucine and the like, ammonium salts, and others.

In addition, the present invention also includes various hydrates or solvates, and any of crystalline polymorphs of the compound of the formula (I) and a pharmaceutically acceptable salt thereof. Also, the present invention includes compounds labeled with various radioactive or non-radioactive isotopes.

(Production Processes)

The compound of the formula (I) and a pharmaceutically acceptable salt thereof can be prepared by applying various known synthetic methods, using the characteristics based on their basic skeletons or the kind of substituents. At this time, depending on the type of the functional groups, it is in some cases effective, from the viewpoint of the preparation techniques, to substitute the functional group with an appropriate protective group (a group which is capable of being easily converted into the functional group), during the stage of starting material or intermediate. Examples of the protective group include the protective groups described in "Protective Groups in Organic Synthesis (4th edition, 2007)", written by Greene and Wuts, and the like, which may be appropriately selected and used depending on reaction conditions. In these methods, a desired compound can be obtained by introducing the protective group to carry out the reaction, and then, if desired, removing the protective group.

In addition, the prodrug of the compound of the formula (I) can be prepared by introducing a specific group during the stage of starting material or intermediate, in the same manner as for the aforementioned protective groups, or by carrying out the reaction using the obtained compound of the formula (I). The reaction can be carried out by applying a method known to a person skilled in the art, such as common esterification, amidation, dehydration, and the like.

Hereinbelow, the representative production processes for the compound of the formula (I) will be described. Each of the production processes may also be carried out with reference to the References appended in the explanation. Further, the production processes of the present invention are not limited to the examples as shown below.

(Production Process 1)

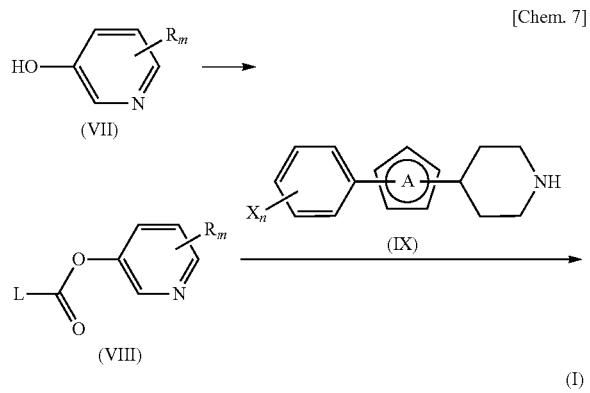

(In the formula, L represents a leaving group).

The compound of the formula (I) can be obtained by converting a compound (VII) to a carbonic acid ester derivative (VIII), which is then reacted with an amine compound (IX).

Here, examples of the leaving group include Cl, imidazolyl, phenoxy, and 4-nitrophenoxy group.

The first step is carried out by reacting the compound (VII) with an equivalent amount or an excess amount of a carbonylating reagent in the presence of a base under from cooling to heating, preferably at −20° C. to 80° C. in a solvent inert to the reaction, usually for about 0.1 hours to one day. In the next step, with no treatment of the reaction of the first step, an equivalent amount or an excess amount of the amine compound (IX) is added to the reaction mixture, and the mixture is subjected to a reaction under from cooling to heating, preferably at −20° C. to 80° C. for about 0.1 hour to one day. The solvent used herein is not particularly limited, but examples thereof include halogenated hydrocarbons such as dichloromethane (DCM), 1,2-dichloroethane (DCE), chloroform, and the like, aromatic hydrocarbons such as benzene, toluene, xylene, and the like, ethers such as diethyl ether, tetrahydrofuran (THF), dioxane, dimethoxyethane (DME), and the like, N,N-dimethylformamide (DMF), dimethylsulfoxide (DMSO), ethyl acetate, acetonitrile, or a mixture thereof. Examples of the carbonyling reagent include diphosgene, triphosgene, 1,1'-carbonyldiimidazole (CDI), 4-nitrophenyl chloroformate, phenyl chloroformate, and the like.

When the carbonic acid ester derivative (VIII) which is an intermediate is stable, this may be first isolated, and then subjected to the next reaction. Further, for the reaction employed in this production process, reference can be made to the following publication.

"Organic Functional Group Preparations", written by S. R. Sandler and W. Karo, 2nd Edition, Vol. 2, Academic Press Inc., 1991

(Production Process 2)

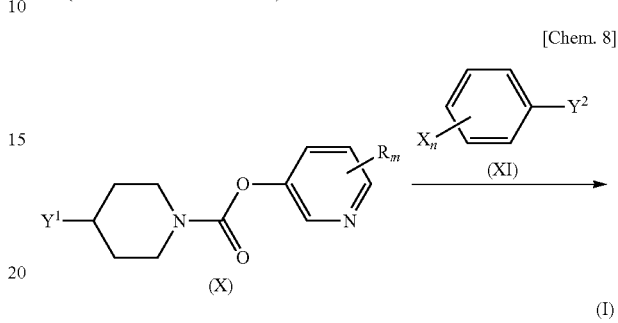

(In the formula, one of $Y^1$ and $Y^2$ represents, for example, a group selected from —$CO_2H$, —$CONH_2$, —$CONH$—$NH_2$, —$N_3$, —OH, and the like, and thus, the other represents a group selected from —C(=N—OH)—$NH_2$, —C(=O)NH—$NH_2$, —C(=O)—$CH_2$—Br, ethynyl group, and the like. The same shall apply hereinafter.)

The present production process is a method in which a compound (X) is reacted with a compound (XI) to synthesize the Ring A, thereby preparing the compound of the formula (I). The compound of the formula (I) can be prepared by selecting a suitable kind of $Y^1$ and $Y^2$ according to a desired Ring A using a known azole ring synthesis method. For example, when the compound of the formula (I), in which the Ring A is 1,2,4-oxadiazole-3,5-diyl, is prepared, the compound (X) and the compound (XI), in which $Y^1$ is —$CO_2H$ and $Y^2$ is —C(=N—OH)—$NH_2$, can be used. Further, when the Ring A is 1,3,4-oxadiazole-2,5-diyl, —$CO_2H$ and —C(=O)NH—$NH_2$ can be used as $Y^1$ and $Y^2$, respectively. Further, when the Ring A is 1,2,3-triazole-1,4-diyl, —$N_3$ and an ethynyl group can be used as $Y^1$ and $Y^2$, respectively. Further, when the Ring A is 1,3-oxazole-2,4-diyl, —$CONH_2$ and —C(=O)—$CH_2$—Br can be used as $Y^1$ and $Y^2$, respectively. Further, when the Ring A is tetrazole-2,5-diyl, tetrazol-3-yl and —OH can be used as $Y^1$ and $Y^2$, respectively. Moreover, for various methods of synthesizing azole ring, reference can be made to the following publication.

Heterocyclic Compounds, New Edition, Applications, written by Hiroshi Yamanaka, Tohru Hino, Masako Nakagawa, and Takao Sakamoto, published by Kodansha Ltd., Scientific, 2004

(Production Process 3)

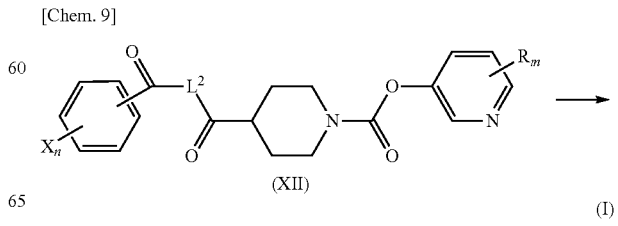

(In the formula, $L^2$ represents a divalent linking chain having 1 to 2 atoms relevant to the length of the chain, and is, for example, —HN—NH—, —$CH_2$—NH—, or methylene. The same shall apply hereinafter.)

The present production process is a method in which a Ring A is synthesized by an intramolecular ring-closing reaction of a compound (XII), and thus, the compound of the formula (I) is prepared. For example, the compound of the formula (I), in which the Ring A is pyrazole-3,5-diyl, can be prepared by reacting the compound (XII) in which $L^2$ is methylene in the presence of hydrazine monohydrate. Further, the compound of the formula (I), in which the Ring A is 1,3,4-oxadiazole-2,5-diyl, can be prepared by reacting the compound (XII) in which $L^2$ is —HN—NH— under basic conditions using tosyl chloride. Further, the compound of the formula (I), in which the Ring A is 1,3-oxazole-2,5-diyl, can be prepared by reacting the compound (XII) in which $L^2$ is —$CH_2$—NH— in the presence of phosphorous oxychloride. In this connection, for various methods for synthesizing azole ring, reference can be made to the following publication.

Heterocyclic Compounds, New Edition, Applications, written by Hiroshi Yamanaka, Tohru Hino, Masako Nakagawa, and Takao Sakamoto, published by Kodansha, Ltd., Scientific, 2004

(Starting Material Syntheses)

Starting Material Production Process 1

[Chem. 10]

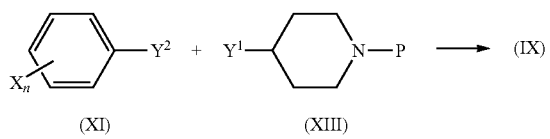

(In the formula, P represents a protecting group of an amino group, and it is, for example, a tert-butoxycarbonyl group. The same shall apply hereinafter.)

The amine compound (IX) can be prepared by reacting a compound (XI) with a compound (XIII) to form the Ring A, and removing the protecting group of the amino group. As $Y^1$ and $Y^2$, the same group as in Production Process 2 above can be used according to the kind of the targeted Ring A.

Starting Material Production Process 2

[Chem. 11]

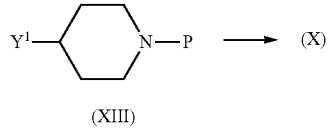

A compound (X) can be prepared by removing the protecting group of the amino group of the compound (XIII), which is then reacted with the compound (VIII) described above. The reaction can be carried out in the same manner as in Production Process 1 described above.

Starting Material Production Process 3

[Chem. 12]

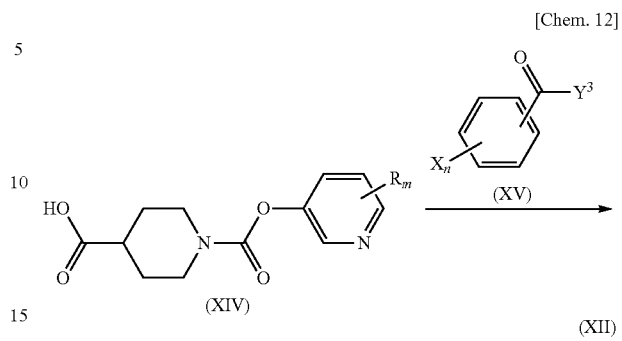

A compound (XII) can be prepared by reacting a compound (XIV) with a compound (XV). As $Y^3$, a suitable substituent is selected according to the kind of $L^2$ of the compound (XII). For example, when $L^2$ of the compound (XII) is methylene, methyl can be used as $Y^3$, when $L^2$ is —HN—NH—, —NH—$NH_2$ can be used as $Y^3$, and when $L^2$ is —$CH_2$—NH—, —$CH_2$—$NH_2$ can be used as $Y^3$.

The compound of the formula (I) can be isolated and purified as its free compound, pharmaceutically acceptable salt, hydrate, solvate, or crystalline polymorphorous substance. The pharmaceutically acceptable salt of the compound of the formula (I) can be prepared by subjecting the compound to a conventional salt formation reaction.

Isolation and purification can be carried out by employing general chemical operations such as extraction, fractional crystallization, various types of fractional chromatography, and the like.

Various isomers can be separated by selecting an appropriate starting compound or by making use of the difference in the physicochemical properties among the isomers. For example, the optical isomers can be lead into each stereochemically pure isomer by means of general optical resolution methods (for example, by fractional crystallization converting the compound into diastereomer salts with optically active bases or acids, by chromatography using a chiral column or the like, and others). Further it can also be prepared from an appropriate optically active starting compound.

The pharmacological activity of the compound of the present invention was confirmed by the following tests.

Test Example 1: Screening for FAAH Activity-Inhibiting Substance Using Human Bladder Epithelial Cancer-Derived Cell:

(1) Screening for FAAH Activity-Inhibiting Substance:

Human bladder epithelial cancer-derived cell line 5637 cells (HTB-9; ATCC) were seeded on a 48-well cell culture plate in an amount of $1\times10^5$ cells/well, using 10% fetal bovine serum (HyClone)-containing RPMI1640 medium (Invitrogen). After being cultured at 37° C. for 12 hours or longer, the cells were washed with 400 μl/well of a buffer (Hank's Balanced Salt Solution, 20 mM Hepes-NaOH (pH 7.4)). A test substance dissolved in DMSO was added to a substrate solution (the above buffer containing 3 radiolabeled anandamide (Anandamide [ethanolamine 1-$^3$H]) and 10 anandamide) so as to have a concentration of from 0.003 nM to 30 nM. As a control, DMSO alone was added. 100 μl/well of the substrate solution was added to the above cells, and incubated in a $CO_2$ incubator at 37° C. for 30 minutes. Then, the cell culture plate was transferred onto ice; the substrate solution was removed by suction; and 75 μl/well of an ice-cooled solution for cell lysis (the above buffer containing 0.5% Triton X-100, and 10 µM of a compound having FAAH-inhibitory activity, cyclohexylcarbamic acid 3'-carbamoylbiphenyl-3-yl ester (URB597; Cayman chemical; Kathuria et al., Nature Med., Vol. 9, pp. 76-81, 2003)) was added thereto, followed by stirring. The resulting cell lysate in each well was individually transferred into a 1.5 ml sample tube, to which was added 150 µl of 1:1 (by volume) chloroform/methanol solution, followed by stirring. After centrifugation (15000 rpm, 2 minutes), the decomposed product, ethanolamine (ethanolamine 1-$^3$H) was separated in the upper layer (water/methanol layer) and the unreacted radiolabeled anandamide was separated in the lower layer (chloroform layer). 25 µl of the upper layer was transferred into a 96-well organic solvent-resistant white microplate (PicoPlate-96; Perkin Elmer), 150 µl of Microscint-20 (Perkin Elmer) was added thereto, and this was measured with a microplate scintillation counter (TopCount™; Beckman). As compared with the control, a substance that gave a decreased measurement value was selected as an FAAH activity-inhibiting substance.

(2) Measurement of IC$_{50}$ Value of FAAH Activity-Inhibiting Substance:

A compound dissolved in DMSO to have a concentration of 10 mM was added to the substrate solution so as to have a concentration from 0.003 nM to 30 nM. According to the method described above, the compound was analyzed for its influence on FAAH activity. As a negative control, DMSO was used, and as a positive control, URB597 was added to the substrate solution to have a concentration of 10 µM. With the measured value of the positive control was set as 0%, and the measured value of the negative control was set as 100%, the IC$_{50}$ values of the test substances were obtained.

Test Example 2: Screening for FAAH Activity-Inhibiting Substance Using Tissue Homogenate of Rat Administered with Test Substance:

(1) Administration to Rat and Preparation of Tissue Homogenate:

A test substance suspended in a 0.5% methyl cellulose (MC) solution was orally administered to two 6-week age SD male rats (Japan SLC) at a dose of 1 mg/kg. As a control, a 0.5% MC solution was orally administered to two rats. After 60 minutes, the rat was sacrificed by decapitation under ether anesthesia, and then the right brain was collected therefrom.

To the collected rat brain was added 2 mL of an ice-cooled buffer (50 mM Tris-HCl (pH 8.0), 1 mM EDTA), and this was homogenized with a homogenizer in ice to give a uniform solution. Further, using an ultrasonic wave generator (UR-20P (Power dial 4), Tommy Seiko), this was subjected to ultrasonic fragmentation for 5 seconds. The protein concentration of the obtained homogenates was measured according to a dye-binding method (protein assay CBB solution; Nacalai Tesque Inc.). Using a buffer (50 mM Hepes (pH 7.4), 1 mM EDTA), the homogenates of the brain tissue of the rat were diluted so that their protein concentration was 60 µg/ml, thereby preparing enzyme solutions.

(2) Measurement of FAAH Activity:

To 200 µl of the enzyme solution was added 50 µl of a substrate solution (2 µM fluorescence-labeled anandamide (Arachidonyl-AMC) (BIOMOL), 50 mM Hepes (pH 7.4), 1 mM EDTA, and 0.5 mg/mL BSA), followed by a reaction at room temperature for 90 minutes. This was measured with a microplate scintillation counter (TopCount™; Beckman).

With the FAAH activity of the control rat not administered with the test substance was set as 100%, and the FAAH activity of the tissue homogenate-free buffer (50 mM Hepes (pH 7.4), 1 mM EDTA) being was set as 0%, the relative value (%) of the FAAH activity of the tissue homogenate of the rat administered with the test substance was determined.

The presence of a therapeutic effect for neuropathic pain may be confirmed by methods known to those skilled in the art or by methods modified from them. For example, using an L5/L6 spinal nerve ligated rat that is produced according to partial modification of a Kim and Chung's method (Pain, Vol. 50, pp. 355-363, 1992), the improving effect of a compound for significant reduction in the response threshold to tactile stimulation (allodynia) can be evaluated, and based on it, the effect for treating neuropathic pain may be confirmed.

Test Example 3: Antiallodynia Effect of Compound in L5/L6 Spinal Nerve-Ligated Rat (Neuropathic Pain Model):

A 5 to 6-week age male SD rat was subjected to the operation of ligating its left-side L5 and L6 spinal nerves with silk threads, under pentobarbital anesthesia. For evaluating the analgesic effect, a von Frey hair test was employed. That is, the hindlimb of the animal was picked with hair, whereupon the minimum strength of the hair which caused limb withdrawal response was referred to as the response threshold to the mechanical stimulation (log gram). In the preliminary test, it was confirmed that the response threshold of the paw of the animal of the operated side was noticeably lowered (under allodynia) within from 7th day to 14th days after the operation, and the antiallodynia effect of the test compound was evaluated on any day within from 7th day to 14th day after the operation. On the day before the day when the test compound would be tested, the response threshold before test compound administration was measured. The test animals were grouped so that the mean value difference between the groups and fluctuation within the groups in the response threshold before test compound administration could be small. In the evaluation test of the test compounds, the response threshold after test compound administration was measured. 3 mg/kg of the test compound was orally administered 60 minutes before the response threshold measurement. With the response threshold of operated and non-operated paws in the solvent-administered group was set as 0% and 100%, respectively, the potency of the test compound for its antiallodynia effect (recovery rate) was calculated.

For several representative compounds of the present invention, the test results of Test Example 1 (IC$_{50}$ values) and the test results of Test Example 3 (recovery rate) are shown below. In this connection, in the table, "-" means being not measured.

TABLE 1

| Ex | IC$_{50}$ (nM) | Recovery rate (%) |
|---|---|---|
| 1 | 0.30 | — |
| 2 | 0.11 | 71 |
| 3 | 0.077 | 81 |
| 14 | 0.85 | — |
| 15 | 0.35 | 97 |
| 9 | 2.2 | — |
| 97 | 0.20 | — |
| 31 | 1.8 | 98 |
| 108 | 0.70 | — |
| 102 | 0.43 | 74 |
| 42 | 0.56 | 97 |
| 43 | 0.98 | 86 |
| 60 | 2.6 | 117 |
| 50 | 0.38 | 119 |
| 72 | 0.11 | 90 |
| 73 | 0.15 | — |
| 69 | 1.40 | — |
| 76 | 0.067 | — |
| 136 | 0.16 | — |
| 79 | 0.047 | — |

TABLE 1-continued

| Ex | IC$_{50}$ (nM) | Recovery rate (%) |
|---|---|---|
| 144 | — | 94 |
| 140 | — | 83 |
| Comparative compound A | 0.58 | 47 |

Comparative compound A: Compound of Example 126 in Patent Document 3

As a result of the tests above, it was shown that the compound of the formula (I) has an FAAH inhibitory activity and is effective in models with neuropathic pain. Therefore, the compound of the formula (I) can be used as an agent for preventing and/or treating various FAAH-related diseases. Further, it can be used, inter alia, as an agent for treating neuropathic pain.

A pharmaceutical composition containing one or two or more kinds of the compound of the formula (I) or a pharmaceutically acceptable salt thereof as an active ingredient can be prepared in accordance with a generally used method, using a pharmaceutical carrier, a pharmaceutical excipient, or the like, that is usually used in the art.

The administration can be carried out through any mode of oral administration via tablets, pills, capsules, granules, powders, liquid preparations, or the like, or parenteral administration via injections such as intraarticular, intravenous, intramuscular, or others, suppositories, eye drops, eye ointments, percutaneous liquid preparations, ointments, percutaneous patches, transmucosal liquid preparations, transmucosal patches, inhalations, and the like.

Regarding solid composition for oral administration, tablets, powders, granules, or the like are used. In such a solid composition, one or two or more active ingredients are mixed with at least one inactive excipient such as lactose, mannitol, glucose, hydroxypropylcellulose, microcrystalline cellulose, starch, polyvinyl pyrrolidone, magnesium aluminometasilicate, and/or the like. According to a conventional method, the composition may contain inactive additives such as lubricants such as magnesium stearate and the like, disintegrators such as sodium carboxymethyl starch and the like, stabilizers, and solubilizing agents. Tablets or pills may be coated with sugar coating, or with a film of gastric or enteric substance if necessary.

The liquid composition for oral administration includes pharmaceutically acceptable emulsions, solutions, suspensions, syrups, elixirs, or the like, and contains a generally used inert diluent, such as purified water or ethanol. In addition to the inert diluent, the liquid composition may contain adjuvants such as solubilizing agents, moistening agents, and suspending agents, sweeteners, flavors, aromatics, and antiseptics.

Injections for parenteral administration include sterile, aqueous or non-aqueous solutions, suspensions, or emulsions. As the aqueous solvent, for example, distilled water for injection or physiological saline is included. Examples of the non-aqueous solvent include propylene glycol, polyethylene glycol, vegetable oils such as olive oil and the like, alcohols such as ethanol and the like, Polysorbate 80 (Pharmacopeia), etc. Such a composition may further contain tonicity agents, antiseptics, moistening agents, emulsifying agents, dispersing agents, stabilizers, or solubilizing agents. These are sterilized, for example, by filtration through a bacteria-retaining filter, blending with bactericides, or irradiation. In addition, these can also be used by producing sterile solid compositions, and dissolving or suspending it in sterile water or a sterile solvent for injection prior to their use.

The agent for external use includes ointments, plasters, creams, jellies, cataplasms, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

Regarding transmucosal agents such as inhalations, transnasal agents, and the like, agents in solid, liquid or semi-solid state are used, and they can be prepared in accordance with conventionally known methods. For example, known excipients, as well as pH adjusting agents, antiseptics, surfactants, lubricants, stabilizers, thickeners, or the like may be appropriately added thereto. For their administration, appropriate devices for inhalation or insufflation may be used. For example, a compound may be administered alone or as powders of formulated mixture, or as solution or suspension by combining it with pharmaceutically acceptable carriers, using conventionally known devices or sprayers, such as a measured administration inhalation device and the like. The dry powder inhalers or the like may be for single or multiple administration use, and dry powders or powder-containing capsules may be used. Alternatively, this may be in a form of a pressurized aerosol spray which uses an appropriate propellant such as chlorofluoroalkane or hydrofluoroalkane, or a suitable gas such as carbon dioxide, or the like.

In the case of oral administration, it is appropriate that the daily dose may be usually from about 0.001 to 100 mg/kg, preferably from 0.1 to 30 mg/kg, and more preferably 0.1 to 10 mg/kg per body weight, and this is administered in a single portion or divided into 2 to 4 portions. Also, in the case of intravenous administration, the appropriate daily dose is from about 0.0001 to 10 mg/kg per body weight, and administration is made once a day or two or more times a day. In addition, a transmucosal agent is administered at a dose from about 0.001 to 100 mg/kg per body weight, once a day or two or more times a day. The dose is appropriately determined in response to an individual case by taking the symptoms, age, and sex, and the like into consideration.

The compound of the formula (I) can be used in combination with various therapeutic agents or prophylactic agents for the diseases, in which the compound of the formula (I) is considered effective, as described above. The combined preparation may be administered simultaneously; or separately, and continuously or at a desired time interval. The preparations to be co-administered may be a blend, or prepared individually.

EXAMPLES

Hereinbelow, the production processes for the compound of the formula (I) will be described in more detail with reference to Examples. In this connection, the present invention is not limited to the compounds described in Examples below. Also, the production processes for the starting material compounds are shown in Preparation Examples. Further, the production processes for the compound of the formula (I) are not limited to the production processes of the specific Examples shown below, and the compound of the formula (I) can be prepared in accordance with a combination of such production processes, or methods apparent to those skilled in the art.

Preparation Example 1

Under ice-cooling, to a mixture of tert-butyl 4-(4-phenyl-1,3-thiazol-2-yl)piperidine-1-carboxylate (5.79 g) and DCM (30 mL) was added 4 M hydrogen chloride/dioxane (30 mL), followed by stirring for 3 hours. The resulting solid was collected by filtration, washed with diisopropyl ether, and then dried under reduced pressure to obtain 4-(4-phenyl-1,3-thiazol-2-yl)piperidine hydrochloride (4.51 g).

Preparation Example 2

To a mixture of tert-butyl 4-(aminocarbonothionyl)piperidine-1-carboxylate (500 mg) and DMF (5 mL) was added 2-bromo-1-(4-chlorophenyl)ethanone (573 mg), followed by stirring at room temperature for 2 hours, and the solvent was evaporated under reduced pressure. To the residue were added water and ethyl acetate, and the organic phase was separated. The organic phase was washed with water and saturated brine, and then dried over magnesium sulfate. The solvent was evaporated under reduced pressure, and the residue was dried under reduced pressure. To the residue were added DCM (6 mL), and under ice-cooling, 4 M hydrogen chloride/dioxane (6 mL), followed by warming to room temperature and then stirring for 4 hours. The solvent was evaporated under reduced pressure, diisopropyl ether and a small amount of methanol were added to the residue, and the resulting solid was collected by filtration. The solid was washed with diisopropyl ether and then dried under reduced pressure to obtain 4-[4-(4-chlorophenyl)-1,3-thiazol-2-yl]piperidine hydrochloride (437 mg).

Preparation Example 3

A mixture of diisopropylamine (3.23 g) and THF (20 mL) was cooled to 0° C., and 1.57 M n-butyllithium/hexane (20.4 mL) was slowly added thereto, followed by stirring at the same temperature for 1 hour. Then, the mixture was cooled to −70° C., and acetophenone (3.84 g) was added dropwise thereto, followed by stirring at the same temperature for 1 hour (reaction liquid 1). Meanwhile, to a suspension of 1-[(pyridin-3-yloxy)carbonyl]piperidine-4-carboxylic acid (2.0 g) in THF (30 mL) was added CDI (1.56 g), followed by stirring at room temperature for 1 hour (reaction liquid 2). The reaction liquid 2 was cooled to −70° C., and the reaction liquid 1 was added dropwise thereto, followed by stirring at the same temperature for 1 hour. Then, the mixture was warmed to 0° C. and then warmed to room temperature. To the reaction liquid was added 0.1 M hydrochloric acid (50 mL), then water and ethyl acetate were added thereto, and the organic phase was separated. The organic phase was washed with water and saturated brine, and then dried over magnesium sulfate. The solvent was evaporated under reduced pressure, and the residue was purified by silica gel column chromatography (chloroform/methanol=100/0 to 90/10) to obtain pyridin-3-yl 4-(3-oxo-3-phenylpropanoyl)piperidine-1-carboxylate (0.93 g).

Preparation Example 4

To a mixture of 1-[(pyridin-3 yloxy)carbonyl]piperidine-4-carboxylic acid (1.5 g) and DCM (15 mL) were added 1-hydroxybenzotriazole (HOBt) (0.85 g), benzohydrazine (0.86 g), and 1-ethyl-3-(3-dimethylaminopropyl)-carbodiimide (WSC) hydrochloride (1.21 g), followed by stirring at room temperature for about 15 hours. To the reaction liquid were added chloroform and water, and the organic phase was separated. The organic phase was washed with water and saturated brine, and dried over magnesium sulfate. The solvent was evaporated under reduced pressure, and the residue was purified by silica gel column chromatography (chloroform/methanol=100/0 to 90/10). To the purified product were added diisopropyl ether and methanol, and the resulting solid was collected by filtration and dried under reduced pressure to obtain pyridin-3-yl 4-[(2-benzoylhydrazino)carbonyl]piperidine-1-carboxylic acid (1.22 g).

Preparation Example 5

Under ice-cooling, to a mixture of ethylbenzenecarboxyimidate hydrochloride (4.58 g) and ethanol (50 mL) was added sodium ethoxide (1.68 g), followed by stirring at the same temperature for about 20 minutes. Then, at the same temperature, tert-butyl 4-(hydrazinecarbonyl)piperidine-1-carboxylate (5.0 g) was added thereto, followed by warming to room temperature, then stirring for 1 hour, and heating and refluxing for 1 day. After leaving to be cooled, the solvent was evaporated under reduced pressure, and the residue was purified by silica gel column chromatography (chloroform/methanol=100/0 to 90/10). To the purified product were added methanol and diisopropyl ether, and the resulting solid was collected by filtration and dried under reduced pressure to obtain tert-butyl 4-(3-phenyl-1H-1,2,4-triazol-5-yl)piperidine-1-carboxylate (2.53 g).

Preparation Example 6

To a mixture of pyridin-3-yl 4-hydroxypiperidine-1-carboxylate (330 mg), triethylamine (0.25 mL) and DCM (7 mL) was added slowly dropwise methanesulfonic acid chloride (0.13 mL) at room temperature. After stirring overnight, the reaction liquid was purified directly by silica gel column chromatography (hexane/ethyl acetate=50/50 to 0/100) to obtain pyridin-3-yl 4-[(methylsulfonyl)oxy]piperidine-1-carboxylate (390 mg) as a colorless solid.

Preparation Example 7

To a solution of tert-butyl 4-[amino(hydroxyimino)methyl]piperidine-1-carboxylate (3.0 g) in THF (30 mL) were added 3,5-difluorobenzoyl chloride (2.4 g) and triethylamine (3.44 mL) under ice-cooling, followed by stirring at room temperature for 2 hours. To the reaction liquid were added ethyl acetate and water, and the organic phase was separated. The organic phase was washed with water and saturated brine, and dried over anhydrous magnesium sulfate, and the solvent was evaporated under reduced pressure. To the residue were added THF (25 mL) and a 1 M tetrabutylammonium fluoride/THF solution (12.4 mL), followed by stirring at 50° C. for 30 minutes. The reaction liquid was concentrated under reduced pressure, and the residue was purified by silica gel column chromatography (chloroform). To the purified product was added diisopropyl ether, and the resulting solid was collected by filtration and dried to obtain tert-butyl 4-[5-(3,5-difluorophenyl)-1,2,4-oxadiazol-3-yl]piperidine-1-carboxylate (4.22 g) as an orange solid.

Preparation Example 8

A mixture of tert-butyl 4-(hydrazinocarbonyl)piperidine-1-carboxylate (1.0 g), 4-chlorobenzonitrile (1.7 g), potassium carbonate (0.28 g), and butanol (8.0 mL) was heated at 150° C. for 2 hours using a microwave device. After leaving to be cooled, the solvent was evaporated under reduced pressure, and the residue was azeotroped with toluene. The residue was purified by silica gel column chromatography (chloroform/methanol=100/0 to 90/10). To the purified product was added diisopropyl ether, and the resulting solid was collected by filtration and dried under reduced pressure to obtain tert-butyl 4-[3-(4-chlorophenyl)-1H-1,2,4-triazol-5-yl]piperidine-1-carboxylate (0.62 g).

Preparation Example 9

To a solution of 3-phenyl-1H-pyrazole (300 mg) in toluene (15 mL) were added tert-butyl 4-hydroxypiperidine-1-carboxylate (838 mg) and (tributylphosphoranylidene)acetonitrile (1.0 g), followed by stirring at 100° C. for 4 hours. The reaction liquid was concentrated under reduced pressure, and then the residue was purified by silica gel column chromatography (hexane/ethyl acetate=100/0 to 50/50) and purified again by silica gel column chromatography (hexane/ethyl acetate=100/0 to 70/30) to obtain tert-butyl 4-(3-phenyl-1H-pyrazol-1-yl)piperidine-1-carboxylate (475 mg) as a colorless oily substance.

Preparation Example 10

To a solution of 3-(dimethylamino)-2-(4-fluorophenyl)acrylaldehyde (3.0 g) in ethanol (30 mL) was added hydrazine monohydrate (0.90 mL), followed by heating and refluxing for 3 hours. After leaving to be cooled, the solvent was evaporated under reduced pressure until the amount of the reaction liquid was reduced to about a half. Water (20 mL) was added thereto, and the resulting solid was collected by filtration and dried under reduced pressure to obtain 4-(4-fluorophenyl)-1H-pyrazole (2.44 g) as a yellow solid.

Preparation Example 11

To a mixture of 6-methylpyridin-3-ol (1.8 g), CDI (2.64 g), and DMSO (18 mL) were added dropwise isonipecotic acid (4.2 g), and a mixture of DMSO (18 mL) and trifluoroacetic acid (2.5 mL), followed by stirring at room temperature for 1 day. To the reaction liquid were added saturated brine and chloroform, and the organic phase was separated. The organic phase was washed with saturated brine twice and then dried over anhydrous sodium sulfate, and the solvent was concentrated under reduced pressure. To the residue was added diisopropyl ether/methanol, and the resulting solid was collected by filtration and dried to obtain 1-{[(6-methylpyridin-3-yl)oxy]carbonyl}piperidine-4-carboxylic acid (3.51 g) as a colorless solid.

Preparation Example 12

To a mixture of 1-[(pyridin-3-yloxy)carbonyl]piperidine-4-carboxylic acid (500 mg) and DCM (10 mL) were added HOBt (297 mg) and WSC hydrochloride (498 mg), followed by stirring at room temperature for 30 minutes. Then, 2-amino-1-(2-fluorophenyl)ethanone hydrochloride (417 mg) and triethylamine (0.31 mL) were added thereto, followed by stirring at room temperature overnight. The reaction liquid was purified directly by silica gel column chromatography (chloroform/methanol=99/1 to 95/5) to obtain pyridin-3-yl 4-{[2-(2-fluorophenyl)-2-oxoethyl]carbamoyl}piperidine-1-carboxylate (423 mg) as a colorless solid.

Preparation Example 13

A mixture of 1-tert-butyl 4-ethylpiperidine-1,4-dicarboxylate (21 g), hydrazine monohydrate (40 mL), and ethanol (200 mL) was heated and refluxed for 22 hours. After leaving to be cooled, the solvent was evaporated under reduced pressure, to the residue were added saturated brine and ethyl acetate, and the organic phase was separated. The organic phase was dried over magnesium sulfate and the solvent was evaporated under reduced pressure. To the residue was added diisopropyl ether, followed by stirring for 1 hour, and the resulting solid was collected by filtration and dried under reduced pressure to obtain tert-butyl 4-(hydrazinocarbonyl)piperidine-1-carboxylate (17.8 g).

Preparation Example 14

To a mixture of 6-methylpyridin-3-ol (5.00 g) and acetonitrile (44 mL) was added CDI (7.43 g), followed by stirring at room temperature for 1 hour. Then, piperidin-4-ol (4.41 g) and 4 M hydrogen chloride/dioxane (23 mL) were added thereto, followed by stirring at 50° C. overnight. After leaving to be cooled, to the reaction liquid were added water and chloroform, and the organic phase was separated. The organic phase was washed with saturated brine and dried over anhydrous sodium sulfate, and the solvent was evaporated under reduced pressure. The residue was purified by silica gel column chromatography (chloroform/methanol=99/1 to 90/10) to obtain 6-methylpyridin-3-yl-4-hydroxypiperidine-1-carboxylate (8.65 g) as a colorless solid.

Preparation Example 15

To benzyl 4-{[2-(4-fluorophenyl)-2-oxoethyl]carbamoyl}piperidine-1-carboxylate (5.5 g) was added phosphorous oxychloride (20 mL), followed by stirring at 80° C. for 3 hours. After leaving to be cooled, the reaction liquid was concentrated under reduced pressure, and the residue was azeotroped with toluene three times. To the residue were added ethyl acetate and water, and the organic phase was separated. The organic phase was washed with a saturated aqueous sodium bicarbonate and saturated brine in this order, and dried over anhydrous sodium sulfate, and the solvent was evaporated under reduced pressure. The residue was purified by silica gel column chromatography (hexane/ethyl acetate=70/30 to 30/70) to obtain benzyl 4-[5-(4-fluorophenyl)-1,3-oxazol-2-yl]piperidine-1-carboxylate (1.84 g) as a colorless oily substance.

Preparation Example 16

To a solution of benzyl 4-[5-(4-fluorophenyl)-1,3-oxazol-2-yl]piperidine-1-carboxylate (1.84 g) in ethanol (40 mL) was added 10% palladium/carbon (54% wet, 200 mg), followed by stiffing for 6 hours under a hydrogen atmosphere. The catalyst was removed by filtration through Celite, and the filtrate was concentrated under reduced pressure. To the residue were added ethanol and 4 M hydrogen chloride/dioxane (1.45 mL), and concentrated under reduced pressure. To the residue were added ethanol and ethyl acetate, followed by stirring, and the resulting solid was collected by filtration and dried to obtain 4-[5-(4-fluorophenyl)-1,3-oxazol-2-yl]piperidine hydrochloride (1.32 g) as a colorless solid.

Preparation Example 17

A suspension of tert-butyl 4-aminopiperidine-1-carboxylate (3.88 g), oxoacetic acid hydrate (1.48 g), and potassium carbonate (4.46 g) in DMF (60 mL) was stirred at room temperature for 3 hours. Then, 1-{[isocyano(phenyl)methyl]sulfonyl}-4-methylbenzene (3.5 g) was added thereto, followed by stirring at room temperature for 14 hours. The solvent was evaporated under reduced pressure, to the residue were added ethyl acetate and water, and the organic phase was separated. The aqueous phase was extracted with ethyl acetate, the combined organic phase was washed with water and saturated brine, and dried over magnesium sulfate, and the solvent was evaporated under reduced pressure. The residue was purified by silica gel column chromatography (chloroform/methanol=100/0 to 90/10) to obtain tert-butyl 4-(4-phenyl-1H-imidazol-1-yl)piperidine-1-carboxylate (3.1 g).

Preparation Example 18

To a mixture of tert-butyl 4-oxopiperidine-1-carboxylate (10.0 g), benzylhydrazinecarboxylate (16.7 g), DCM (150 mL), and acetic acid (5.75 mL) was added sodium triacetoxyborohydride (31.9 g), followed by stirring at room temperature for 2.5 days. To the reaction liquid was added water, and the organic phase was separated. The aqueous phase was extracted with chloroform, and the combined organic phase was washed with water, a saturated aqueous sodium bicarbonate, and saturated brine in this order, and dried over magnesium sulfate, and the solvent was evaporated under reduced pressure. The residue was purified by silica gel column chromatography (chloroform/methanol=100/0 to 90/10) to obtain tert-butyl 4-{2-[(benzyloxy)carbonyl]hydrazino}piperidine-1-carboxylate (10.0 g).

Preparation Example 19

To a mixture of tert-butyl 4-oxopiperidine-1-carboxylate (10.0 g) and ethanol (100 mL) was added 5% palladium/carbon (2.0 g), followed by stirring under a hydrogen atmosphere for about 2 hours. The catalyst was removed by filtration, and the solvent was evaporated under reduced pressure. The residue was purified by silica gel column chromatography (chloroform/methanol=100/0 to 90/10) to obtain tert-butyl 4-hydrazinopiperidine-1-carboxylate (4.1 g).

Preparation Example 20

To a mixture of 2-methylpyridin-3-yl-4-{[2-(tert-butoxycarbonyl)hydrazino]carboxyl}piperidine-1-carboxylate (11.98 g) and DCM (100 mL) was added 4 M hydrogen chloride/dioxane (100 mL), followed by stirring at room temperature for about 15 hours. The solvent was evaporated under reduced pressure, and the residue was dissolved in methanol/water (10/1). Potassium carbonate (8.75 g) was added thereto, followed by stirring for about 3 hours. The solvent was evaporated under reduced pressure, and to the residue was added chloroform, followed by drying over magnesium sulfate. The solvent was evaporated under reduced pressure, and the residue was dried under reduced pressure to obtain 2-methylpyridin-3-yl 4-(hydrazinocarbonyl)piperidine-1-carboxylate (7.49 g).

Preparation Example 21

To a mixture of 2,3-difluorobenzonitrile (5.00 g) and ethanol (55 mL) was added dropwise acetyl chloride (35 mL) under ice-cooling, followed by stirring at room temperature for 7 days. The reaction liquid was concentrated under reduced pressure, and to the residue was added diisopropyl ether, followed by stirring for 1 hour. The resulting solid was collected by filtration and dried to obtain ethyl 2,3-difluorobenzenecarboximidate hydrochloride (4.68 g) as a white solid.

Preparation Example 22

To a mixture of tert-butyl 4-[(2-benzoylhydrazino)carbonyl]piperidine-1-carboxylate (3.00 g) and THF (60 mL) were added triethylamine (7.2 mL) and toluenesulfonyl chloride (4.94 g), followed by stirring at 50° C. overnight. The reaction liquid was concentrated under reduced pressure, and the residue was purified by silica gel column chromatography (hexane/ethyl acetate=95/5 to 80/20) to obtain tert-butyl 4-(5-phenyl-1,3,4-oxadiazol-2-yl)piperidine-1-carboxylate (2.84 g) as a colorless oily sub stance.

Preparation Example 23

To a mixture of 1-(tert-butoxycarbonyl)piperidine-4-carboxylic acid (5.0 g) and toluene (50 mL) was added CDI (3.9 g), followed by stirring at room temperature for 3 hours. Then, N'-hydroxybenzenecarboxyimidate (3.3 g) was added thereto, followed by stirring for 1.5 hours and then heating and refluxing for 2 hours. After leaving to be cooled, to the reaction liquid were added ethyl acetate and water, and the organic phase was separated. The organic phase was washed with water and saturated brine, and dried over magnesium sulfate, and the solvent was evaporated under reduced pressure. To the residue were added hexane and ethyl acetate, and the resulting solid was collected by filtration to obtain tert-butyl 4-(3-phenyl-1,2,4-oxadiazol-5-yl)piperidine-1-carboxylate (5.46 g).

Preparation Example 24

A mixture of tert-butyl 4-(3-oxo-3-phenylpropanoyl)piperidine-1-carboxylate (3.1 g), hydrazine monohydrate (0.5 mL), ethanol (30 mL), and THF (30 mL) was stirred at room temperature for about 15 hours, and at 60° C. for 1 hour. Hydrazine monohydrate (0.5 mL) was further added thereto, followed by stirring again at 60° C. for 3 hours. Hydrazine monohydrate (4.0 mL) was added thereto again, followed by stirring at 60° C. for 8 hours. After leaving to be cooled, the solvent was evaporated under reduced pressure, and to the residue were added diisopropyl ether and methanol, followed by stirring. The resulting solid was collected by filtration and dried under reduced pressure to obtain tert-butyl 4-(3-phenyl-1H-pyrazol-5-yl)piperidine-1-carboxylate (2.46 g).

Preparation Example 25

To a solution of tert-butyl 4-hydrazinopiperidine-1-carboxylate (646 mg) and ethanol (15 mL) was added phenyl malonaldehyde (444 mg), followed by stirring at 75° C. for about 1.5 days. The reaction liquid was concentrated under reduced pressure, and the residue was purified by silica gel column chromatography (hexane/chloroform-50/50 to 0/100) to obtain tert-butyl 4-(4-phenyl-1H-pyrazol-1-yl)piperidine-1-carboxylate (226 mg).

Preparation Example 26

A mixture of tert-butyl 4-[(2-oxo-2-phenylethyl)carbamoyl]piperidine-1-carboxylate (5.0 g) and ammonium trifluoroacetate (18.9 g) was stirred at an exterior temperature of 170° C. for 30 minutes. After leaving to be cooled, water and chloroform were added thereto, and the aqueous phase was separated. The aqueous phase was adjusted to a pH of about 10 with a 24% aqueous sodium hydroxide, and extracted with chloroform. The combined organic phase was washed with water and saturated brine, and dried over magnesium sulfate, and the solvent was evaporated under reduced pressure. The residue was dried under reduced pressure, and dissolved in DCM (20 mL) and methanol (10 mL), and 4 M hydrogen chloride/dioxane (5.3 mL) was added thereto. The solvent was concentrated under reduced pressure, to the residue was added diisopropyl ether/methanol, and the resulting solid was collected by filtration, and dried under reduced pressure to obtain 4-(4-phenyl-1H-imidazol-2-yl)piperidine dihydrochloride (3.29 g).

Preparation Example 27

To a solution of 2,5-difluorobenzoic acid (1.95 g) in THF (40 mL) were added oxalyl chloride (1.5 mL) and a catalytic amount of DMF, followed by stirring at room temperature for 1 hour. The reaction liquid was concentrated under reduced pressure, and to the residue was added THF (40 mL). Under ice-cooling, tert-butyl 4-[amino(hydroxyimino)methyl]piperidine-1-carboxylate (2.5 g) and triethylamine (3.0 mL) were added thereto, followed by stirring at room temperature for 2 hours. To the reaction liquid were added ethyl acetate and water, and the organic phase was separated. The organic phase was washed with water and saturated brine, and dried over anhydrous magnesium sulfate, and the solvent was evaporated under reduced pressure. To a solution of the residue in THF (20 mL) was added a 1 M tetrabutylammonium fluoride/THF solution (10.3 mL), followed by stirring at 50° C. for 30 minutes. The reaction liquid was concentrated under reduced pressure, and the residue was purified by silica gel column chromatography (chloroform). To the purified product was added 4 M hydrogen chloride/dioxane (40 mL), followed by stirring at room temperature for 2 hours. The reaction liquid was concentrated under reduced pressure, then to the residue was added THF, and the resulting solid was collected by filtration. The solid was washed with THF and ethyl acetate in this order, and dried under reduced pressure to obtain 4-[5-(2,5-difluorophenyl)-1,2,4-oxadiazol-3-yl]piperidine hydrochloride (2.58 g).

Preparation Example 28

To a suspension of 3-(4-fluorophenyl)-1H-1,2,4-triazole (700 mg) in toluene (15 mL) were added tert-butyl 4-hydroxypiperidine-1-carboxylate (1.3 g) and (tributylphosphoranylidene)acetonitrile (2.0 g), followed by stirring at 110° C. for 15 hours. The reaction liquid was concentrated under reduced pressure, and the residue was purified by silica gel column chromatography (chloroform/methanol=100/0 to 97/3). To the purified product was added 4 M hydrogen chloride/dioxane (15 mL), followed by stirring at room temperature for 16 hours. To the reaction liquid wad added ethyl acetate, and the resulting solid was collected by filtration, and dried under reduced pressure to obtain 4-[3-(4-fluorophenyl)-1H-1,2,4-triazol-1-yl]piperidine hydrochloride (422 mg).

Preparation Example 29

To a mixture of 1-(tert-butoxycarbonyl)piperidine-4-carboxylic acid (5.0 g) and DCM (50 mL) were added HOBt (3.09 g), 4-fluorobenzohydrazine (3.53 g), and WSC hydrochloride (5.02 g), followed by stirring at room temperature overnight. To the reaction liquid was added ethyl acetate, followed by washing with water/saturated brine (1:1), a saturated aqueous sodium bicarbonate, and saturated brine in this order, and drying over anhydrous sodium sulfate, and the solvent was evaporated under reduced pressure. To the residue were added THF (160 mL), p-toluenesulfonyl chloride (8.32 g), and triethylamine (12 mL), followed by stirring at 60° C. overnight. The reaction liquid was concentrated under reduced pressure, and the residue was purified by silica gel column chromatography (hexane/ethyl acetate=90/10 to 50/50) to obtain tert-butyl 4-[5-(4-fluorophenyl)-1,3,4-oxadiazol-2-yl]piperidine-1-carboxylate (5.83 g) as a pale brown solid.

By the same production processes as for the compounds of Preparation Examples 1 to 29 described above, the compounds of Preparation Examples as shown in Tables to be described later were prepared using each of the corresponding starting materials. The structures, the production processes, and the physicochemical data of the compounds of Preparation Examples are shown in Tables 2 to 11 to be described later.

Example 1

By the same procedure as in Preparation Example 14 described above, pyridin-3-yl 4-(4-phenyl-1,3-thiazol-2-yl)piperidine-1-carboxylate hydrochloride was obtained from 4-(4-phenyl-1,3-thiazol-2-yl)piperidine hydrochloride.

Example 2

By the same procedure as in Preparation Example 24 described above, pyridin-3-yl 4-(3-phenyl-1H-pyrazol-5-yl)piperidine-1-carboxylate was obtained from pyridin-3-yl-4-(3-oxo-3-phenylpropanoyl)piperidine-1-carboxylate.

Example 3

By the same procedure as in Preparation Example 22 described above, pyridin-3-yl 4-[3-(4-fluorophenyl)-1,2,4-oxadiazol-5-yl]piperidine-1-carboxylate was obtained from 1-[(pyridin-3-yloxy)carbonyl]piperidine-4-carboxylic acid.

Example 4

To a mixture of 1-[(pyridin-3-yloxy)carbonyl]piperidine-4-carboxylic acid (300 mg), 4-fluorobenzohydrazide (222 mg), HOBt (170 mg), and DCM (6 mL) was added WSC hydrochloride (299 mg), followed by stirring at room temperature overnight. The reaction liquid was purified directly by silica gel column chromatography (chloroform/methanol=99/1 to 90/10). The residue was dissolved in THF (6 mL), and toluenesulfonyl chloride (686 mg) and triethylamine (1.0 mL) were added thereto, followed by stirring at 50° C. for 8 hours. The reaction liquid was concentrated under reduced pressure, and the residue was purified by silica gel column chromatography (hexane/ethyl acetate=70/30 to 0/100). To the purified product were added isopropanol/water, and the resulting solid was collected by filtration and dried to obtain pyridin-3-yl 4-[5-(4-fluorophenyl)-1,3,4-oxadiazol-2-yl]piperidine-1-carboxylate (224 mg) as a colorless solid.

Example 5

By the same procedure as in Preparation Example 22 described above, pyridin-3-yl 4-(5-phenyl-1,3,4-oxadiazol-2-yl)piperidine-1-carboxylate was obtained from pyridin-3-yl 4-[(2-benzoylhydrazino)carbonyl]piperidine-1-carboxylate.

Example 6

To a mixture of pyridin-3-yl 4-[(methylsulfonyl)oxy]piperidine-1-carboxylate (221 mg) and DMSO (4 mL) was added sodium azide (96 mg), followed by stirring at 60° C. for 8 hours. The reaction liquid was diluted with ethyl acetate, and washed with water and saturated brine in this order. The organic phase was dried over anhydrous sodium sulfate, the solvent was evaporated under reduced pressure, and the residue was purified by silica gel column chromatography (hexane/ethyl acetate=70/30 to 0/100). To the purified product (149 mg) and a solution of ethynylbenzene (0.066 mL) in tert-butanol (10 mL) were added water (2 mL), sodium ascorbate (12 mg), and copper (II) sulfate (1.5 mg), followed by stirring overnight. The reaction liquid was diluted with ethyl acetate, and washed with water and saturated brine. The organic phase was dried over anhydrous sodium sulfate, the solvent was concentrated under reduced pressure, and the residue was purified by silica gel column chromatography (chloroform/methanol=99/1 to 90/10). To the purified product were added diisopropyl ether/ethyl acetate, followed by stirring, and the resulting solid was collected by filtration and dried to obtain pyridin-3-yl 4-(4-phenyl-1H-1,2,3-triazol-1-yl)piperidine-1-carboxylate (165 mg) as a colorless solid.

Example 7

A mixture of 6-methylpyridin-3-yl 4-carbamoyl piperidine-1-carboxylate (500 mg), 2-bromo-1-phenylethanone (453 mg), and N,N-dimethylacetamide (5 mL) was stirred at 130° C. for 3 days. After leaving to be cooled, ethyl acetate and water/a saturated aqueous sodium bicarbonate (1:1) were added thereto, followed by stirring for 1 hour, and the reaction liquid was filtered. The organic phase of the filtrate was separated out, washed with water/saturated brine (1:1) and saturated brine in this order, and dried over anhydrous sodium sulfate. The solvent was evaporated under reduced pressure and the residue was purified by silica gel column chromatography (chloroform/methanol=99/1 to 95/5). The purified product was dissolved in ethanol, and an excess amount of 4 M hydrogen chloride/dioxane was added thereto. The reaction liquid was concentrated under reduced pressure and dried to obtain 6-methylpyridin-3-yl 4-(4-phenyl-1,3-oxazol-2-yl)piperidine-1-carboxylate hydrochloride (134 mg) as a pale brown amorphous substance.

Example 8

By the same procedure as in Preparation Example 15 described above, pyridin-3-yl 4-[5-(2-fluorophenyl)-1,3-oxazol-2-yl]piperidine-1-carboxylate dihydrochloride was obtained from pyridin-3-yl 4-{[2-(2-fluorophenyl)-2-oxoethyl]carbamoyl}piperidine-1-carboxylate.

Example 9

To a mixture of pyridin-3-yl 4-hydroxypiperidine-1-carboxylate (300 mg), 5-phenyl-1H-tetrazole (217 mg), triphenyl phosphine (460 mg), and THF (3 mL) was added dropwise a 2.2 M solution of diethyl azodicarboxylate in toluene (0.8 mL), followed by stirring at room temperature overnight. The reaction liquid was concentrated under reduced pressure, and the residue was purified by silica gel column chromatography (chloroform/methanol=99/1 to 90/10), and purified again by silica gel column chromatography (hexane/ethyl acetate=70/30 to 0/100). To the purified product was added hexane/ethyl acetate, followed by stirring, and then the resulting solid was collected by filtration and dried to obtain pyridin-3-yl 4-(5-phenyl-2H-tetrazol-2-yl)piperidine-1-carboxylate (250 mg) as a colorless solid.

Example 10

To a solution of ethyl 2-chlorobenzenecarboxyimidate hydrochloride (435 mg) in ethanol (10 mL) was added sodium methoxide (107 mg), followed by stirring at room temperature for 30 minutes. Then, 2-methylpyridin-3-yl-4-(hydrazinocarbonyl)piperidine-1-carboxylate (500 mg) was added thereto, followed by stirring at 90° C. for 2 days. The reaction liquid was concentrated under reduced pressure, and the residue was purified by silica gel column chromatography (chloroform/methanol=99/1 to 90/10). The purified product was dissolved in ethanol, and an excess amount of 4 M hydrogen chloride/dioxane was added thereto, followed by stirring. The reaction liquid was concentrated under reduced pressure and dried to obtain 2-methylpyridin-3-yl 4-[3-(2-chlorophenyl)-1H-1,2,4-triazol-5-yl]piperidine-1-carboxylate dihydrochloride (289 mg) as a pale yellow solid.

By the same methods as for the compounds of Examples 1 to 10 described above, the compounds of Examples as shown in Tables to be described later were prepared using each of the corresponding starting materials. The structures of the compounds of Examples 1 to 159 are shown in Tables 12 to 31, and their production processes and physicochemical data are shown in Tables 32 to 38.

In addition, the following abbreviations are used in Tables to be described later. Pre: Preparation Example number, Ex: Example number, Str: Structural formula, Syn: Production process (Among the Examples/Preparation Examples above, the Preparation Example number and the Example number, same process of which was used for preparing the compound, is described. Here, P represents Preparation Example and E represents Example. For example, it is represented that the compound of Preparation Example 30 was prepared in the same manner as for the compound of Preparation Example 1, and the compound of Example 11 was prepared in the same manner as for the compound of Example 1), Dat: Physicochemical data (NMR: δ (ppm) in $^1$H NMR in DMSO-$d_6$, FAB+: FAB-MS (cation), FAB−: FAB-MS (anion), ESI+: ESI-MS (cation), ESI−: ESI-MS (anion), EI:EI-MS (cation), CI+: CI-MS (cation), APCI+: APCI-MS (cation)), Me: methyl, Et: ethyl, Bn: benzyl, Boc: tert-butoxycarbonyl, Ms: methanesulfonyl, TsOH: p-toluenesulfonic acid, Z: benzyloxycarbonyl.

TABLE 2

| Pre | Syn | Str | Dat |
|---|---|---|---|
| 1 | P1 | 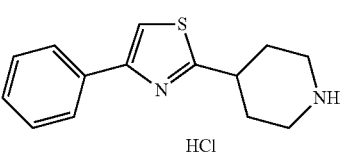 | ESI+: 488.99 [2M + H]+ |

TABLE 2-continued

| Pre | Syn | Str | Dat |
|---|---|---|---|
| 2 | P2 | 4-(4-chlorophenyl)-2-(piperidin-4-yl)thiazole HCl | APCI+: 278.82 [M + H]+ |
| 3 | P3 | pyridin-3-yl 4-(3-oxo-3-phenylpropanoyl)piperidine-1-carboxylate | ESI+: 352.85 [M + H]+ |
| 4 | P4 | pyridin-3-yl 4-(2-benzoylhydrazinecarbonyl)piperidine-1-carboxylate | ESI−: 367.00 [M − H]− |
| 5 | P5 | tert-butyl 4-(5-phenyl-1H-1,2,4-triazol-3-yl)piperidine-1-carboxylate | ESI+: 329.21 [M + H]+ |
| 6 | P6 | pyridin-3-yl 4-(methylsulfonyloxy)piperidine-1-carboxylate | FAB+: 301 [M + H]+ |
| 7 | P7 | tert-butyl 4-(5-(3,5-difluorophenyl)-1,2,4-oxadiazol-3-yl)piperidine-1-carboxylate | FAB+: 366 [M + H]+ |
| 8 | P8 | tert-butyl 4-(5-(4-chlorophenyl)-1H-1,2,4-triazol-3-yl)piperidine-1-carboxylate | ESI+: 363.06 [M + H]+ |
| 9 | P9 | tert-butyl 4-(3-phenyl-1H-pyrazol-1-yl)piperidine-1-carboxylate | FAB+: 328 [M + H]+ |

TABLE 3

| | | | |
|---|---|---|---|
| 10 | P10 | 4-(4-fluorophenyl)-1H-pyrazole | CI+: 163 [M + H]+ |
| 11 | P11 | 1-((6-methylpyridin-3-yloxy)carbonyl)piperidine-4-carboxylic acid | ESI+: 265 [M + H]+ |

TABLE 3-continued

| 12 | P12 | (2-fluorophenyl-CO-CH2-NH-CO-piperidine-N-CO-O-pyridin-3-yl) | ESI+: 386 [M + H]+ |
| 13 | P13 | Boc-piperidine-4-C(O)-NH-NH2 | ESI−: 242.02 [M − H]− |
| 14 | P14 | HO-piperidine-N-C(O)-O-(6-methylpyridin-3-yl) | FAB+: 237 [M + H]+ |
| 15 | P15 | 5-(4-fluorophenyl)-2-(piperidin-4-yl)oxazole, N-Z | ESI+: 381 [M + H]+ |
| 16 | P16 | 5-(4-fluorophenyl)-2-(piperidin-4-yl)oxazole · HCl | ESI+: 247 [M + H]+ |
| 17 | P17 | 4-phenyl-1-(1-Boc-piperidin-4-yl)imidazole | ESI+: 328.09 [M + H]+ |
| 18 | P18 | ZHN-NH-(1-Boc-piperidin-4-yl) | ESI+: 350.19 [M + H]+ |
| 19 | P19 | H2N-NH-(1-Boc-piperidin-4-yl) | ESI+: 116.07 [M + H − C4H8 − CO2]+ |
| 20 | P20 | H2N-NH-C(O)-piperidine-N-C(O)-O-(2-methylpyridin-3-yl) | ESI+: 279.06 [M + H]+ |

TABLE 4

| 21 | P21 | EtO-C(=NH)-(2,3-difluorophenyl) · HCl | ESI+: 186 [M + H]+ |
| 22 | P22 | 2-phenyl-5-(1-Boc-piperidin-4-yl)-1,3,4-oxadiazole | FAB+: 330 [M + H]+ |

TABLE 4-continued
| | | | |
|---|---|---|---|
| 23 | P23 | 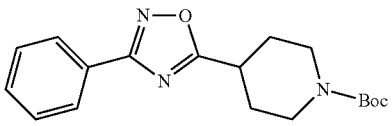 | ESI+: 330.17 [M + H]+ |
| 24 | P24 | 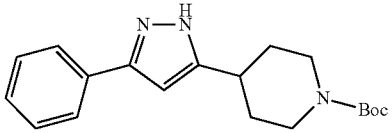 | ESI+: 328.19 [M + H]+ |
| 25 | P25 | 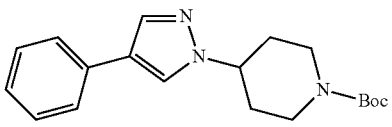 | ESI+: 272.13 [M + H—C$_4$H$_8$]+ |
| 26 | P26 | 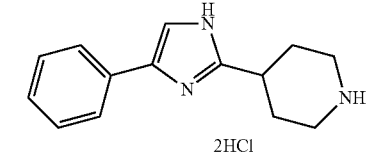 2HCl | ESI−: 226.22 [M − H]− |
| 27 | P27 | 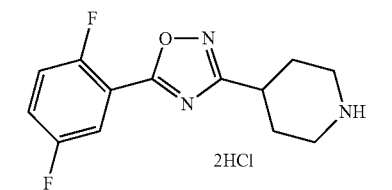 2HCl | ESI+: 266 [M + H]+ |
| 28 | P28 | 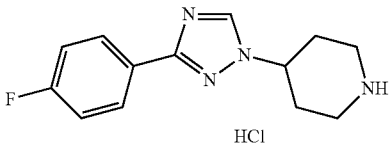 HCl | ESI+: 247 [M + H]+ |
| 29 | P29 | 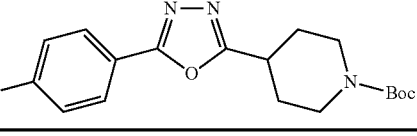 | FAB+: 348 [M + H]+ |
TABLE 5
| | | | |
|---|---|---|---|
| 30 | P1 | 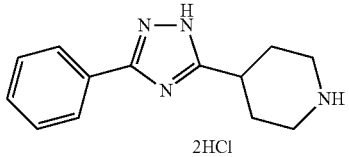 2HCl | ESI+: 229.28 [M + H]+ |
| 31 | P1 | 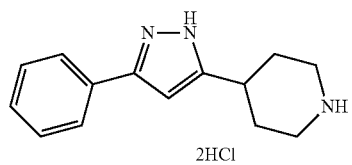 2HCl | FAB+: 230 [M + H]+ |
| 32 | P1 | 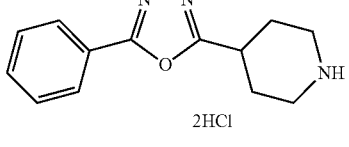 HCl | FAB+: 230 [M + H]+ |
| 33 | P1 | 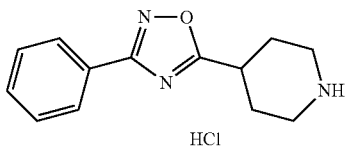 2HCl | ESI+: 228.01 [M + H]+ |
| 34 | P1 | 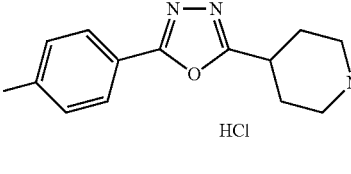 HCl | ESI+: 248 [M + H]+ |

TABLE 5-continued
| 35 | P1 | 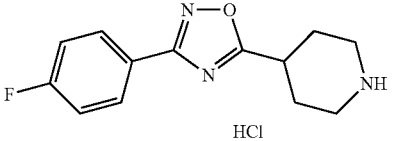 | ESI+: 248 [M + H]+ |
| 36 | P1 | 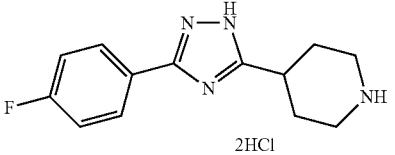 | FAB+: 247 [M + H]+ |
| 37 | P1 | 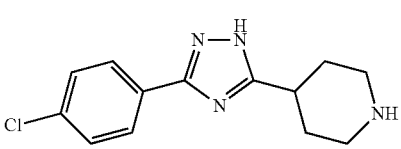 | ESI+: 263.03 [M + H]+ |
TABLE 6
| 38 | P1 | 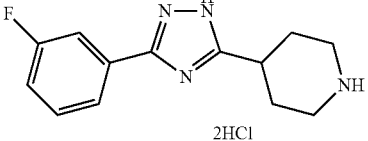 | ESI+: 246.93 [M + H]+ |
| 39 | P1 | 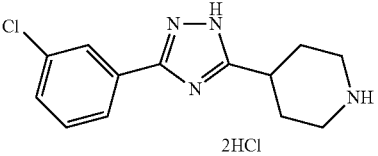 | ESI+: 262.97 [M + H]+ |
TABLE 6-continued
| 40 | P1 | 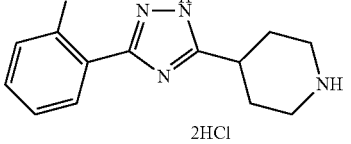 | ESI+: 247.06 [M + H]+ |
| 41 | P1 | 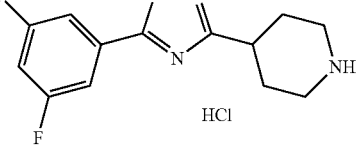 | ESI+: 266 [M + H]+ |
| 42 | P1 | 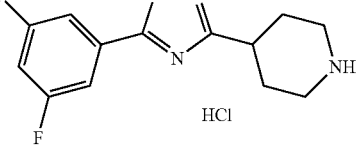 | ESI+: 265.20 [M + H]+ |
| 43 | P1 | 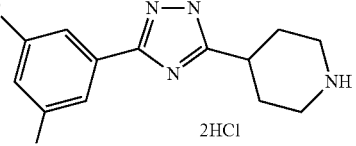 | ESI+: 266 [M + H]+ |
| 44 | P1 | 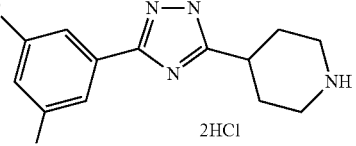 | ESI+: 228.15 [M + H]+ |
| 45 | P1 | 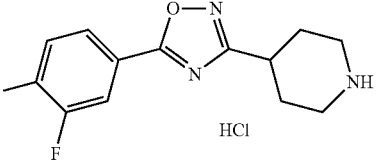 | ESI+: 228 [M + H]+ |
TABLE 7
| 46 | P1 | 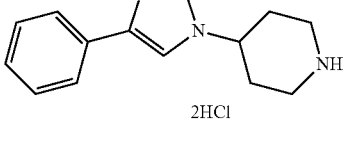 | ESI+: 246 [M + H]+ |
| 47 | P1 | 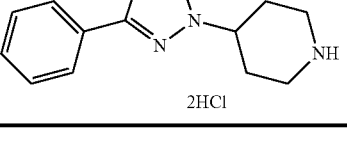 | ESI+: 228.14 [M + H]+ |
| 48 | P1 | 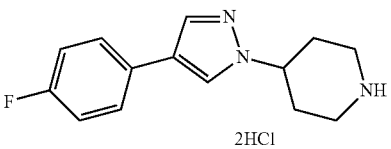 | ESI+: 247.12 [M + H]+ |

TABLE 7-continued
| | | | |
|---|---|---|---|
| 49 | P1 | 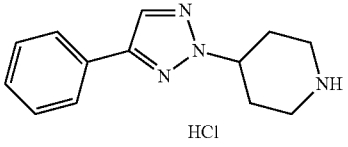 | ESI+: 229.32 [M + H]+ |
| 50 | P1 | 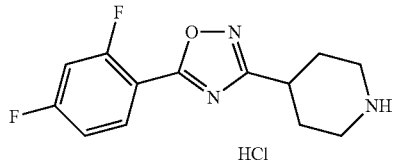 | FAB+: 266 [M + H]+ |
| 51 | P2 | 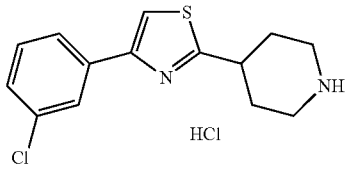 | APCI+: 278.92 [M + H]+ |
| 52 | P2 | 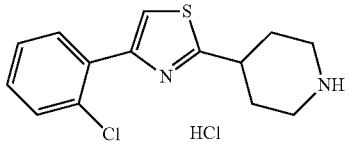 | APCI+: 278.82 [M + H]+ |
| 53 | P3 | 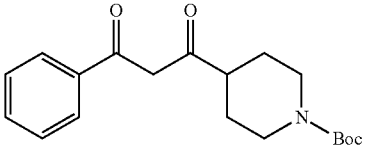 | ESI+: 332.21 [M + H]+ |
TABLE 8
| | | | |
|---|---|---|---|
| 54 | P4 | 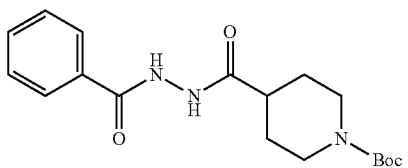 | ESI+: 348.03 [M + H]+ |
| 55 | P5 | 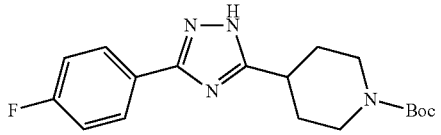 | FAB+: 347 [M + H]+ |
| 56 | P5 | 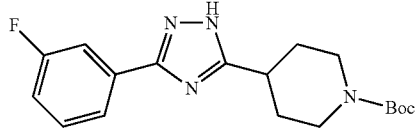 | ESI+: 347.16 [M + H]+ |
| 57 | P5 | 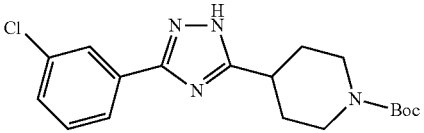 | ESI+: 363.13 [M + H]+ |

TABLE 8-continued
| 58 | P5 | 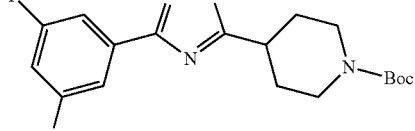 | ESI+: 347.06 [M + H]+ |
| 59 | P6 | | ESI+: 315 [M + H]+ |
| 60 | P6 | | FAB+: 315 [M + H]+ |
| 61 | P7 | | FAB+: 366 [M + H]+ |
| 62 | P7 | | FAB+: 366 [M + H]+ |
TABLE 9
| 63 | P8 | 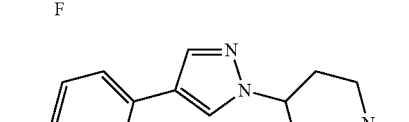 | ESI+: 365.04 [M + H]+ |
| 64 | P9 | 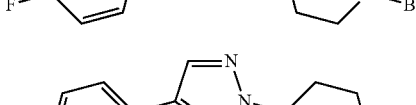 | ESI+: 346 [M + H]+ |
| 65 | P9 | | ESI+: 291.18 [M + H—C$_4$H$_8$]+ |
| 66 | P9 | 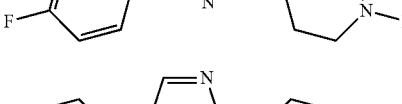 | ESI+: 273.06 [M + H—C$_4$H$_8$]+ |

TABLE 9-continued

| # | Prep | Structure | MS |
|---|---|---|---|
| 67 | P11 | 4-carboxy-piperidine-1-carboxylic acid 2-methylpyridin-3-yl ester | ESI+: 265 [M + H]+ |
| 68 | P12 | tert-butyl 4-{[(2-oxo-2-phenylethyl)carbamoyl]}piperidine-1-carboxylate | ESI+: 347.17 [M + H]+ |
| 69 | P12 | benzyl 4-{[2-(4-fluorophenyl)-2-oxoethyl]carbamoyl}piperidine-1-carboxylate | FAB+: 399 [M + H]+ |
| 70 | P12 | pyridin-3-yl 4-{[2-(3-fluorophenyl)-2-oxoethyl]carbamoyl}piperidine-1-carboxylate | ESI+: 386 [M + H]+ |
| 71 | P12 | 2-methylpyridin-3-yl 4-{[2-(2-fluorophenyl)-2-oxoethyl]carbamoyl}piperidine-1-carboxylate | ESI+: 400 [M + H]+ |

TABLE 10

| # | Prep | Structure | MS |
|---|---|---|---|
| 72 | P12 | 2-methylpyridin-3-yl 4-{[2-(3-fluorophenyl)-2-oxoethyl]carbamoyl}piperidine-1-carboxylate | ESI+: 400 [M + H]+ |
| 73 | P12 | 6-methylpyridin-3-yl 4-{[2-(2-fluorophenyl)-2-oxoethyl]carbamoyl}piperidine-1-carboxylate | ESI+: 400 [M + H]+ |
| 74 | P12 | 6-methylpyridin-3-yl 4-{[2-(3-fluorophenyl)-2-oxoethyl]carbamoyl}piperidine-1-carboxylate | ESI+: 400 [M + H]+ |
| 75 | P12 | 2-methylpyridin-3-yl 4-(2-Boc-hydrazinecarbonyl)piperidine-1-carboxylate | ESI+: 379.08 (M + H)+ |

TABLE 10-continued

| 76 | P12 | *[piperidine structure with Boc-NH-NH-C(O)- group and pyridine-Me ester]* | ESI−: 377.17 [M − H]− |
| 77 | P14 | *[HO-piperidine-N-C(O)-O-pyridine]* | FAB+: 223 [M + H]+ |
| 78 | P14 | *[HO-piperidine-N-C(O)-O-(2-Me-pyridine)]* | ESI+: 237 [M + H]+ |
| 79 | P14 | *[H₂N-C(O)-piperidine-N-C(O)-O-(6-Me-pyridin-3-yl)]* | ESI+:264 [M + H]+ |
| 80 | P14 | *[H₂N-C(O)-piperidine-N-C(O)-O-(2-Me-pyridin-3-yl)]* | ESI+: 264 [M + H]+ |

TABLE 11

| 81 | P20 | *[H₂N-NH-C(O)-piperidine-N-C(O)-O-(6-Me-pyridin-3-yl)]* | ESI+: 279.06 [M + H]+ |
| 82 | P21 | *[3,4-difluorophenyl-C(=NH)-OEt · HCl]* | ESI+: 186 [M + H]+ |
| 83 | P21 | *[2,4-difluorophenyl-C(=NH)-OEt · HCl]* | ESI+: 186 [M + H]+ |
| 84 | P21 | *[4-CF₃-phenyl-C(=NH)-OEt · HCl]* | ESI+: 218 [M + H]+ |
| 85 | P21 | *[3-CF₃-phenyl-C(=NH)-OEt · HCl]* | ESI+: 218 [M + H]+ |

TABLE 11-continued
| 86 | P21 | 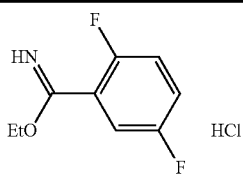 | ESI+: 186 [M + H]+ |
| 87 | P23 | 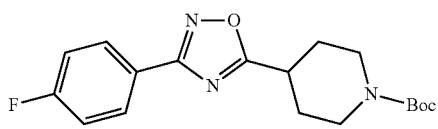 | FAB+: 348 [M + H]+ |
| 88 | P27 | 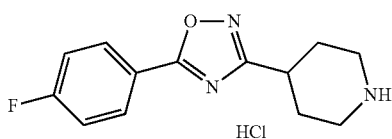 | ESI+: 248 [M + H]+ |
TABLE 12
| Ex | Str |
| --- | --- |
| 1 | 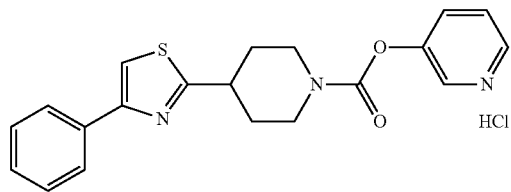 |
| 2 | 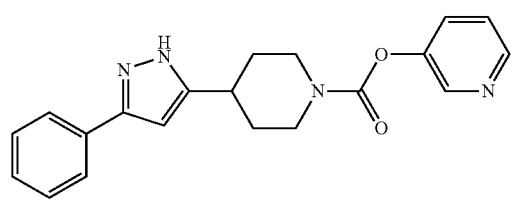 |
| 3 | 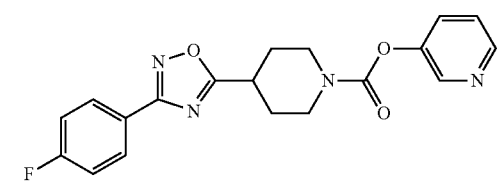 |
| 4 | 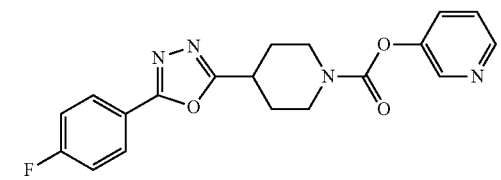 |
| 5 | 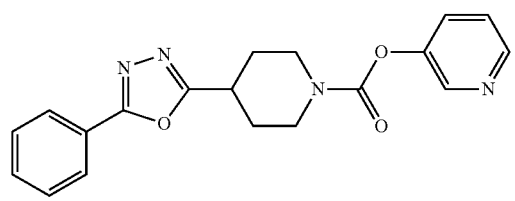 |
TABLE 12-continued
| Ex | Str |
| --- | --- |
| 6 | 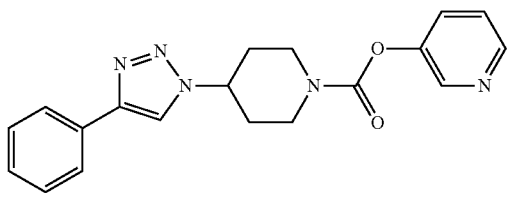 |
| 7 | 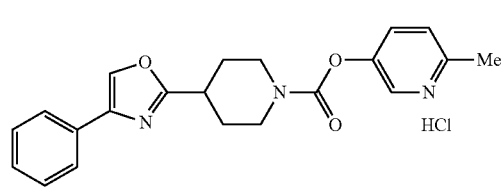 |
TABLE 13
| 8 | 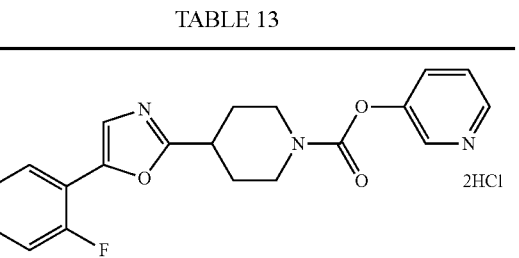 |
| 9 | 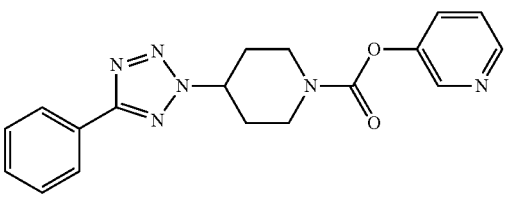 |

TABLE 13-continued
| 10 | 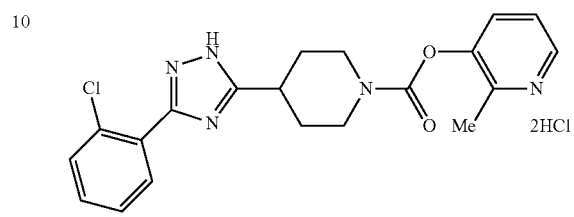 2HCl |
|---|---|
| 11 | 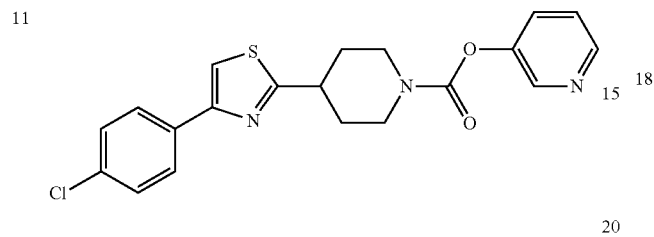 |
| 12 | 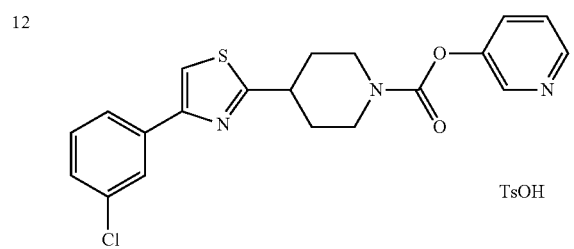 TsOH |
| 13 | 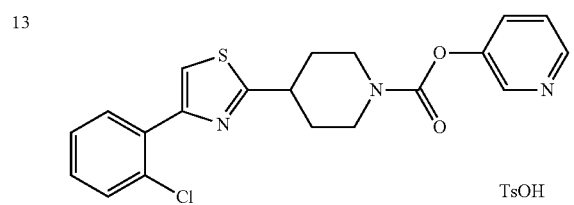 TsOH |
| 14 | 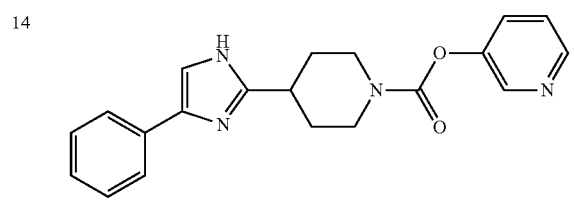 |
TABLE 14
| 15 | 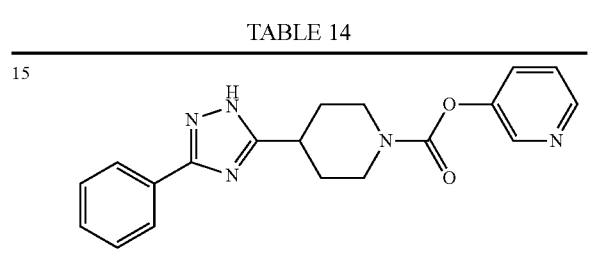 |
| --- | --- |
| 16 | 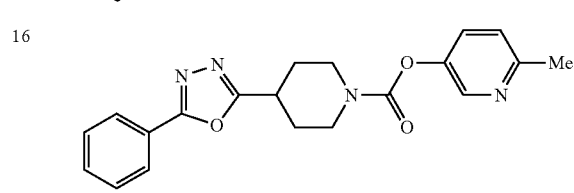 |
TABLE 14-continued
| 17 | 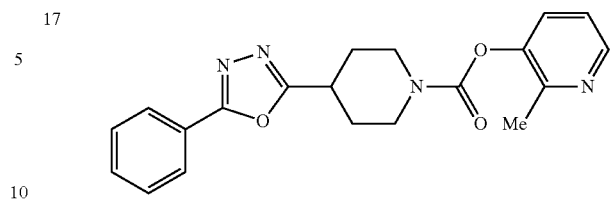 |
|---|---|
| 18 | 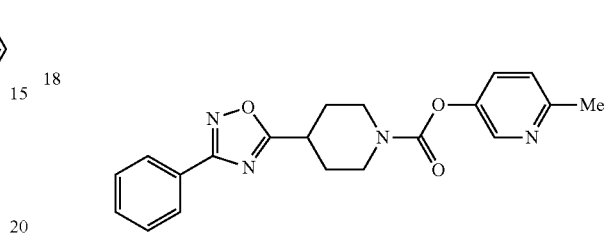 |
| 19 | 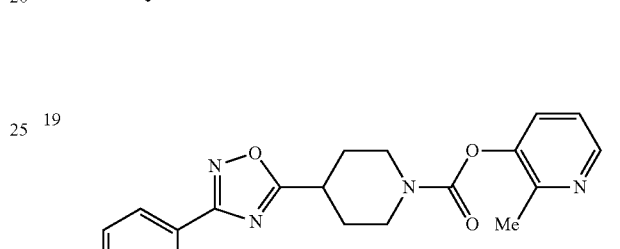 HCl |
| 20 | 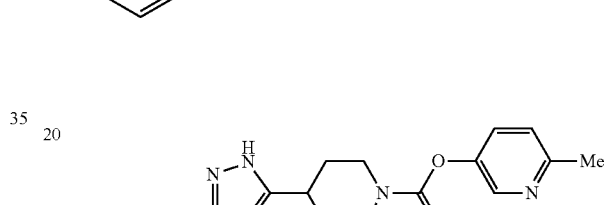 |
| 21 |  |
| 22 | 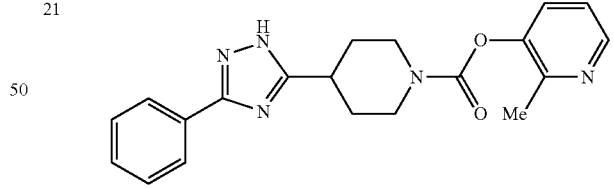 |

TABLE 15
| 23 | 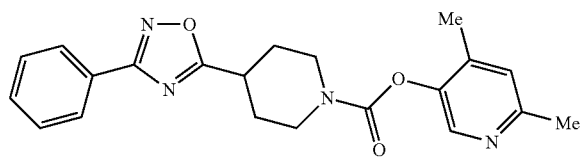 |
| 24 | 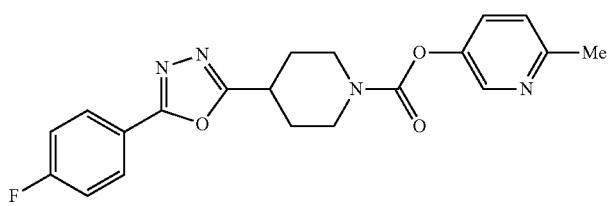 |
| 25 | 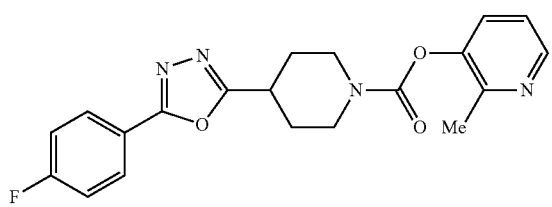 |
| 26 | 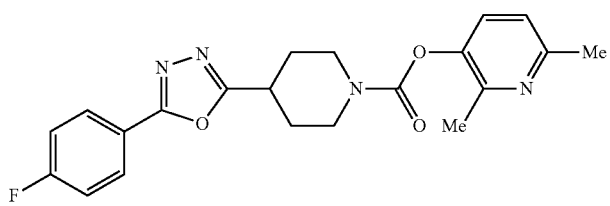 |
| 27 | 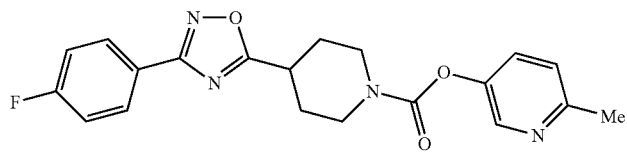 |
| 28 | 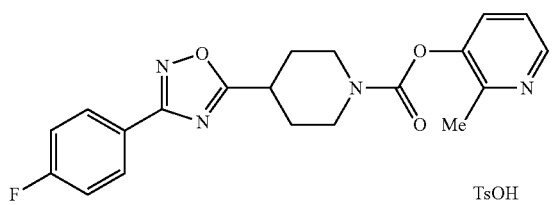 TsOH |
| 29 | 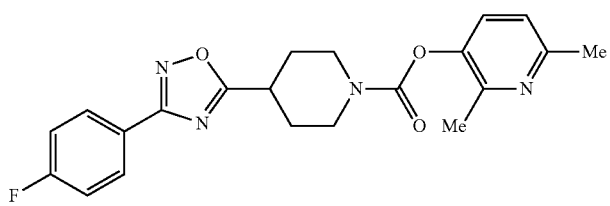 |
| 30 | 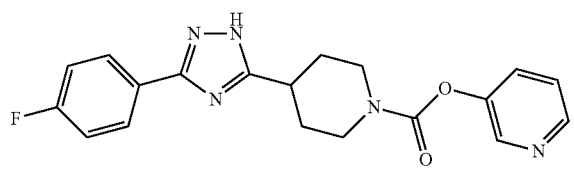 |

TABLE 15-continued
| 31 | 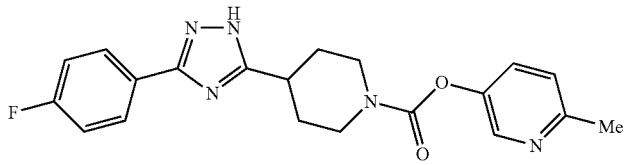 |
TABLE 16
| 32 | 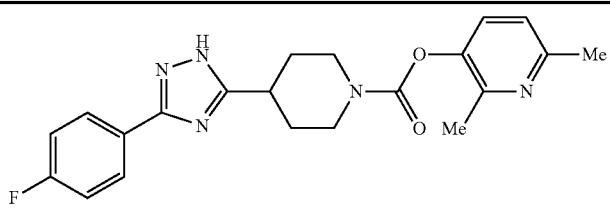 |
| 33 | 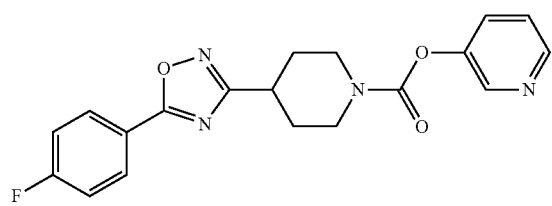 |
| 34 | 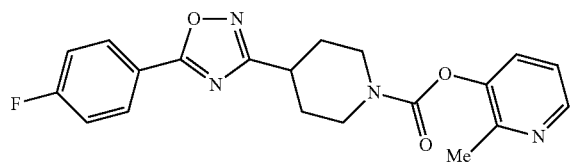 |
| 35 | 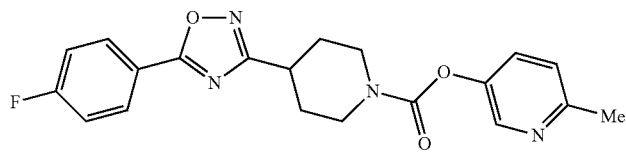 |
| 36 | 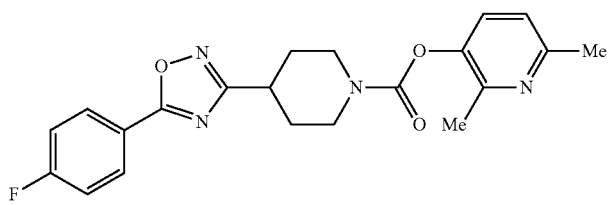 |
| 37 | 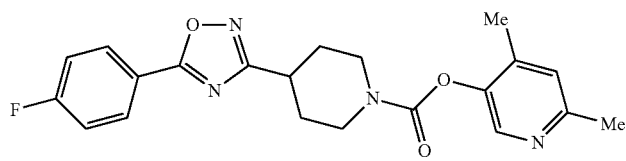 |
| 38 | 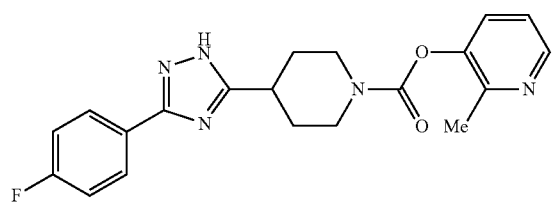 |

TABLE 16-continued

| 39 | [5-(3,5-difluorophenyl)-1,2,4-oxadiazol-3-yl]-piperidine-1-carboxylic acid 6-methylpyridin-3-yl ester |

TABLE 17

| 40 | 5-(3,5-difluorophenyl)-1,2,4-oxadiazol-3-yl piperidine-1-carboxylic acid 2-methoxy-6-methylpyridin-3-yl ester |
| 41 | 5-(4-fluorophenyl)oxazol-2-yl piperidine-1-carboxylic acid pyridin-3-yl ester · HCl |
| 42 | 5-(4-fluorophenyl)oxazol-2-yl piperidine-1-carboxylic acid 6-methylpyridin-3-yl ester |
| 43 | 5-(4-fluorophenyl)oxazol-2-yl piperidine-1-carboxylic acid 2-methoxypyridin-3-yl ester · 2HCl |
| 44 | 5-(2,4-difluorophenyl)-1,2,4-oxadiazol-3-yl piperidine-1-carboxylic acid 6-methylpyridin-3-yl ester |
| 45 | 5-(4-chlorophenyl)-1H-1,2,4-triazol-3-yl piperidine-1-carboxylic acid 6-methylpyridin-3-yl ester |
| 46 | 5-(3-chlorophenyl)-1H-1,2,4-triazol-3-yl piperidine-1-carboxylic acid 6-methylpyridin-3-yl ester |
| 47 | 5-(3-chlorophenyl)-1H-1,2,4-triazol-3-yl piperidine-1-carboxylic acid 2-methoxypyridin-3-yl ester · 2HCl |

TABLE 18

| 48 | 5-(3-fluorophenyl)-1H-1,2,4-triazol-3-yl piperidine-1-carboxylic acid 6-methylpyridin-3-yl ester |
| 49 | 5-(3-fluorophenyl)-1H-1,2,4-triazol-3-yl piperidine-1-carboxylic acid 2-methoxypyridin-3-yl ester |
| 50 | 5-(2-fluorophenyl)-1H-1,2,4-triazol-3-yl piperidine-1-carboxylic acid 2-methoxypyridin-3-yl ester · 2HCl |
| 51 | 5-(2,4-difluorophenyl)-1,2,4-oxadiazol-3-yl piperidine-1-carboxylic acid 2-methoxypyridin-3-yl ester |
| 52 | 5-(2-fluorophenyl)-1H-1,2,4-triazol-3-yl piperidine-1-carboxylic acid 2-methoxy-6-methylpyridin-3-yl ester |
| 53 | 5-(3-fluorophenyl)-1H-1,2,4-triazol-3-yl piperidine-1-carboxylic acid 2-methoxy-6-methylpyridin-3-yl ester |
| 54 | 5-(2,4-difluorophenyl)-1,2,4-oxadiazol-3-yl piperidine-1-carboxylic acid 2-methoxy-6-methylpyridin-3-yl ester |
| 55 | 5-(2,4-difluorophenyl)-1,2,4-oxadiazol-3-yl piperidine-1-carboxylic acid 4,6-dimethylpyridin-3-yl ester |

TABLE 19
| | |
|---|---|
| 56 | 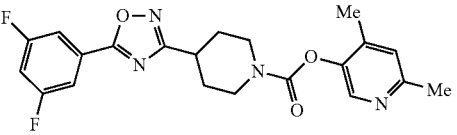 |
| 57 | 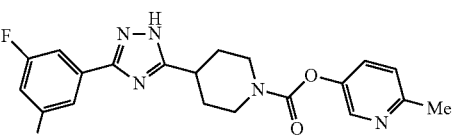 |
| 58 | 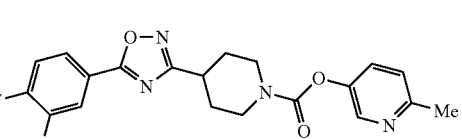 |
| 59 | 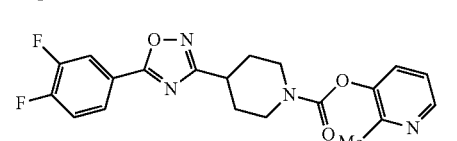 |
| 60 | 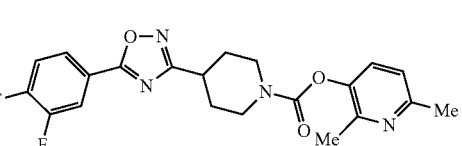 |
| 61 | 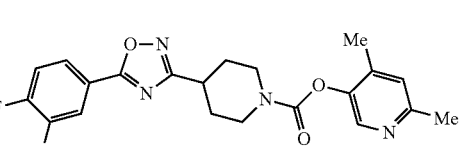 |
| 62 | 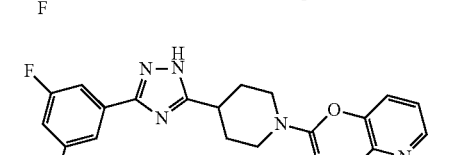 |
TABLE 20
| | |
|---|---|
| 63 | 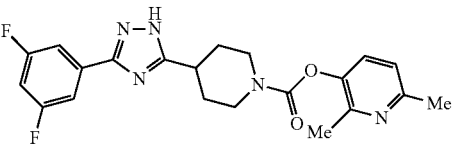 |
| 64 | 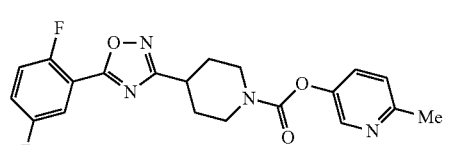 |
| 65 | 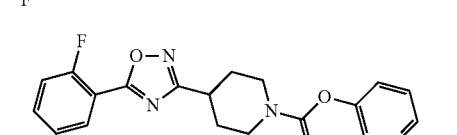 |
TABLE 20-continued
| | |
|---|---|
| 66 | 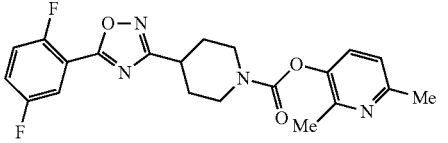 |
| 67 | 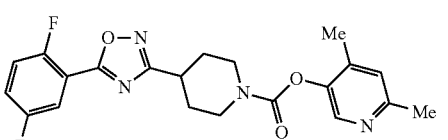 |
| 68 | 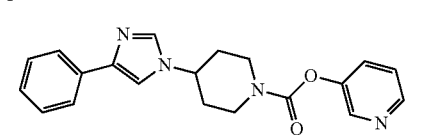 |
| 69 | 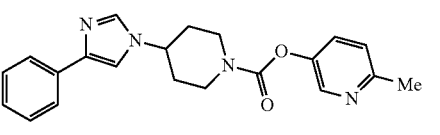 |
| 70 | 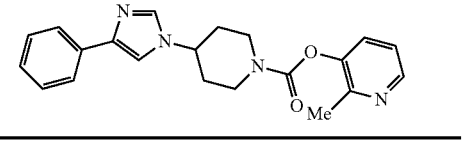 |
TABLE 21
| | |
|---|---|
| 71 | 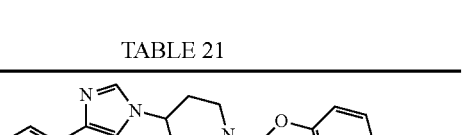 |
| 72 | 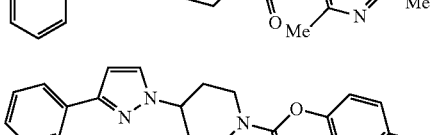 |
| 73 | 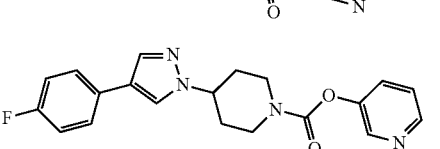 |
| 74 | 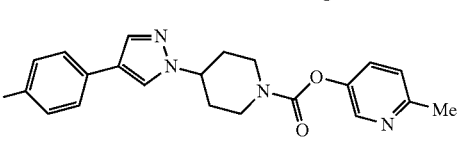 |
| 75 | 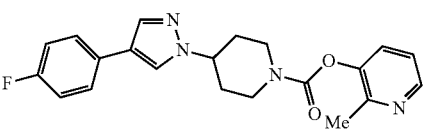 |
| 76 | 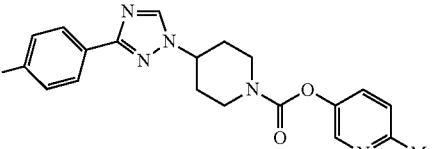 |

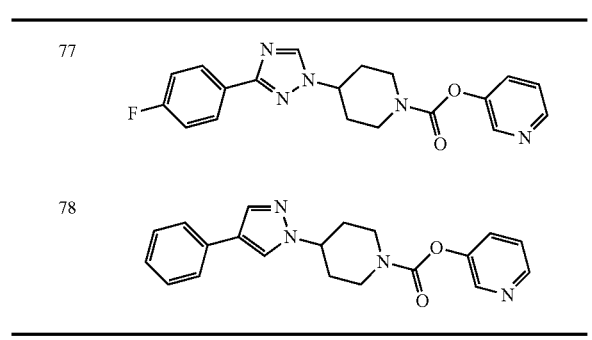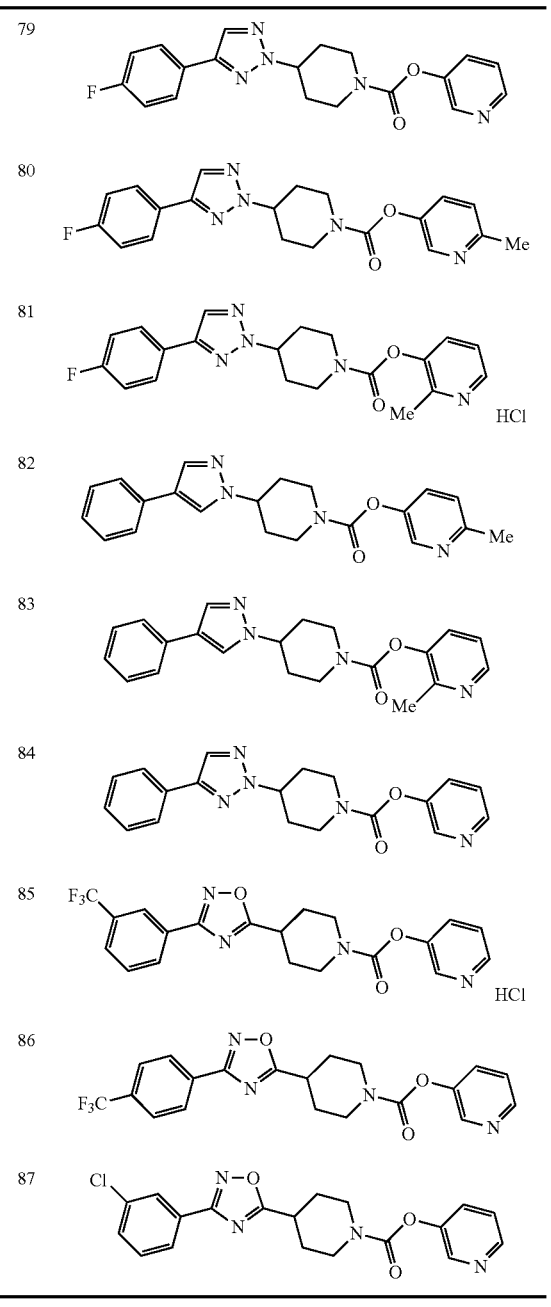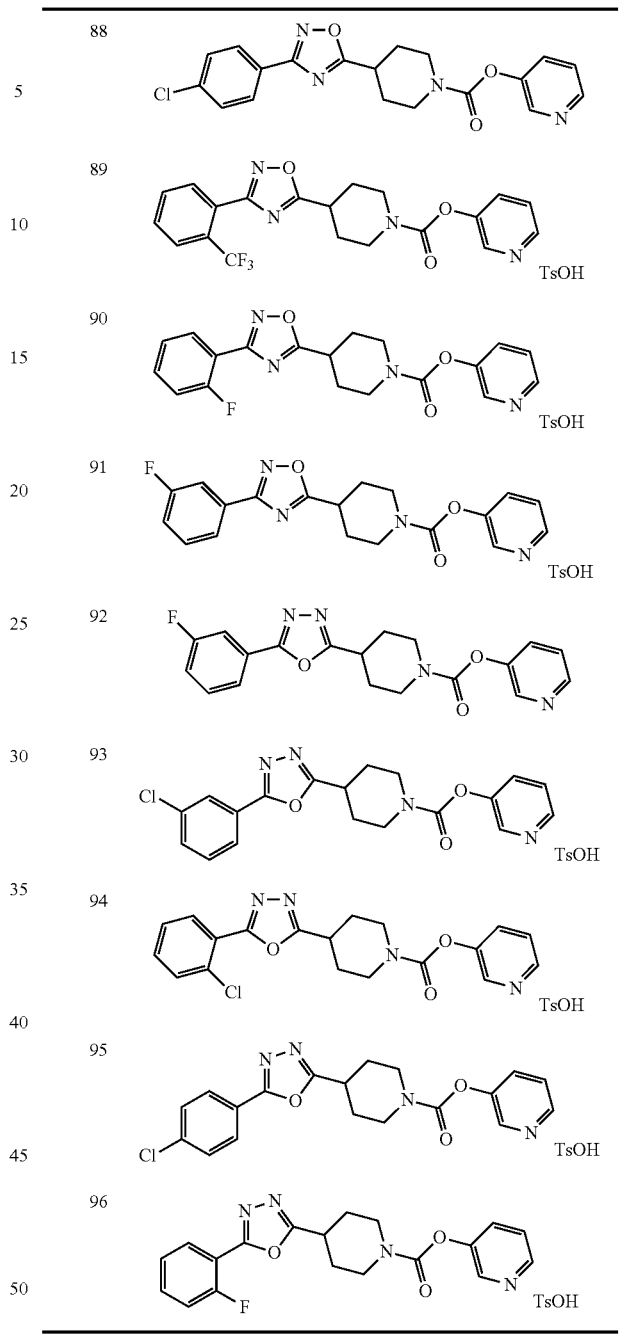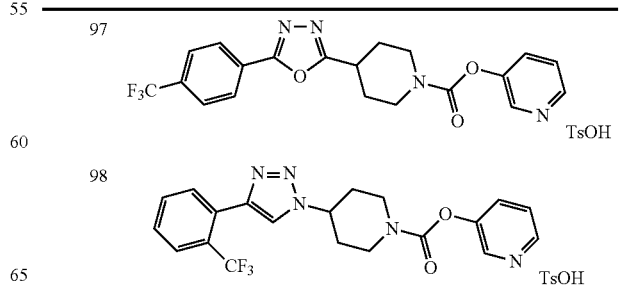

TABLE 24-continued
| | | |
|---|---|---|
| 99 | 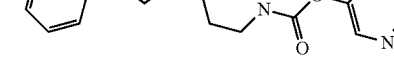 | TsOH |
| 100 | | TsOH |
| 101 | | TsOH |
| 102 | | TsOH |
| 103 | | |
| 104 | | |
TABLE 25
| | |
|---|---|
| 105 | |
| 106 | |
| 107 | |
| 108 | |
| 109 | |
TABLE 25-continued
| | |
|---|---|
| 110 | |
| 111 | |
| 112 | |
TABLE 26
| | |
|---|---|
| 113 | |
| 114 | |
| 115 | |
| 116 | |
| 117 | |
| 118 | |
| 119 | |
| 120 | |

TABLE 27

| | |
|---|---|
| 121 | 3,5-difluorophenyl-triazole-piperidine-carboxylate-(6-methylpyridin-3-yl) |
| 122 | 3,4-difluorophenyl-triazole-piperidine-carboxylate-(6-methylpyridin-3-yl) |
| 123 | 2-fluorophenyl-triazole-piperidine-carboxylate-(2-methylpyridin-3-yl) |
| 124 | 3-fluorophenyl-triazole-piperidine-carboxylate-(2-methylpyridin-3-yl) |
| 125 | 4-fluorophenyl-triazole-piperidine-carboxylate-(2-methylpyridin-3-yl) |
| 126 | 2-chlorophenyl-triazole-piperidine-carboxylate-(2-methylpyridin-3-yl) HCl |
| 127 | 3-chlorophenyl-triazole-piperidine-carboxylate-(2-methylpyridin-3-yl) |
| 128 | 4-chlorophenyl-triazole-piperidine-carboxylate-(2-methylpyridin-3-yl) |

TABLE 28

| | |
|---|---|
| 129 | 2-(trifluoromethyl)phenyl-triazole-piperidine-carboxylate-(2-methylpyridin-3-yl) HCl |
| 130 | 3-(trifluoromethyl)phenyl-triazole-piperidine-carboxylate-(2-methylpyridin-3-yl) HCl |
| 131 | 4-(trifluoromethyl)phenyl-triazole-piperidine-carboxylate-(2-methylpyridin-3-yl) |
| 132 | 2,4-difluorophenyl-triazole-piperidine-carboxylate-(2-methylpyridin-3-yl) |
| 133 | 3,5-difluorophenyl-triazole-piperidine-carboxylate-(2-methylpyridin-3-yl) |
| 134 | 3,4-difluorophenyl-triazole-piperidine-carboxylate-(2-methylpyridin-3-yl) |
| 135 | 3-fluorophenyl-oxazole-piperidine-carboxylate-(6-methylpyridin-3-yl) HCl |
| 136 | 4-chlorophenyl-oxazole-piperidine-carboxylate-(6-methylpyridin-3-yl) |

TABLE 29

| | |
|---|---|
| 137 | 4-fluorophenyl-oxazole-piperidine-carboxylate-(2-methylpyridin-3-yl) 2HCl |
| 138 | phenyl-oxazole-piperidine-carboxylate-(2-methylpyridin-3-yl) HCl |
| 139 | 3-fluorophenyl-oxazole-piperidine-carboxylate-(2-methylpyridin-3-yl) HCl |
| 140 | 4-fluorophenyl-oxazole-piperidine-carboxylate-(6-methylpyridin-3-yl) |
| 141 | 2,4-difluorophenyl-oxazole-piperidine-carboxylate-(6-methylpyridin-3-yl) |
| 142 | 5-phenyl-oxazole-piperidine-carboxylate-pyridin-3-yl |

TABLE 29-continued

| 143 | [5-(2-fluorophenyl)oxazol-2-yl piperidine, 2-methylpyridin-3-yl carbamate] 2HCl |
| 144 | [5-(3-fluorophenyl)oxazol-2-yl piperidine, 2-methylpyridin-3-yl carbamate] HCl |
| 145 | [5-(2-fluorophenyl)oxazol-2-yl piperidine, 6-methylpyridin-3-yl carbamate] HCl |

TABLE 30

| 146 | [5-(3-fluorophenyl)oxazol-2-yl piperidine, 6-methylpyridin-3-yl carbamate] 2HCl |
| 147 | [5-(3-fluorophenyl)oxazol-2-yl piperidine, pyridin-3-yl carbamate] HCl |
| 148 | [5-(3-trifluoromethylphenyl)-1H-1,2,4-triazol-3-yl piperidine, 6-methylpyridin-3-yl carbamate] 2HCl |
| 149 | [5-(2,5-difluorophenyl)-1H-1,2,4-triazol-3-yl piperidine, 6-methylpyridin-3-yl carbamate] |
| 150 | [5-(4-trifluoromethylphenyl)-1H-1,2,4-triazol-3-yl piperidine, 6-methylpyridin-3-yl carbamate] |
| 151 | [5-(4-chlorophenyl)-1H-1,2,4-triazol-3-yl piperidine, 2-methylpyridin-3-yl carbamate] 2HCl |
| 152 | [5-(2,3-difluorophenyl)-1H-1,2,4-triazol-3-yl piperidine, 2-methylpyridin-3-yl carbamate] 2HCl |

TABLE 30-continued

| 153 | [5-(2,4-difluorophenyl)-1H-1,2,4-triazol-3-yl piperidine, 2-methylpyridin-3-yl carbamate] 2HCl |

TABLE 31

| 154 | [5-(2,5-difluorophenyl)-1H-1,2,4-triazol-3-yl piperidine, 2-methylpyridin-3-yl carbamate] 2HCl |
| 155 | [5-(3,4-difluorophenyl)-1H-1,2,4-triazol-3-yl piperidine, 2-methylpyridin-3-yl carbamate] |
| 156 | [5-(3-trifluoromethylphenyl)-1H-1,2,4-triazol-3-yl piperidine, 2-methylpyridin-3-yl carbamate] 2HCl |
| 157 | [5-(4-trifluoromethylphenyl)-1H-1,2,4-triazol-3-yl piperidine, 2-methylpyridin-3-yl carbamate] 2HCl |
| 158 | [5-(2,4-difluorophenyl)-1H-1,2,4-triazol-3-yl piperidine, 6-methylpyridin-3-yl carbamate] |
| 159 | [3-phenyl-1,2,4-oxadiazol-5-yl piperidine, pyridin-3-yl carbamate] |

TABLE 32

| Ex | Syn | Data |
|---|---|---|
| 1 | E1 | NMR: 1.86 (2H, m), 2.20 (2H, m), 3.17 (1H, t, J = 12.4 Hz), 3.34 (1H, t, J = 12.4 Hz), 3.42 (1H, m), 4.12 (1H, d, J = 12.4 Hz), 4.29 (1H, d, J = 13.6 Hz), 7.35 (1H, t, J = 7.3 Hz), 7.45 (2H, t, J = 7.8 Hz), 7.91 (1H, m), 7.97 (2H, d, J = 7.3 Hz), 8.03 (1H, s), 8.25 (1H, d, J = 8.4 Hz), 8.70 (1H, d, J = 5.2 Hz), 8.87 (1H, s); FAB+: 366.1 [M + H]+ |
| 2 | E2 | NMR: 1.70 (2H, m), 2.03 (2H, m), 2.96 (1H, m), 3.07 (1H, m), 3.23 (1H, m), 4.09 (1H, m), 4.25 (1H, m), 6.85 (1H, s), 7.29 (1H, t, J = 7.4 Hz), 7.41 (2H, m), 7.53 (1H, dd, J = 4.8, 8.4 Hz), 7.73 (3H, m), 8.50 (2H, m); ESI+: 349.1 [M + H]+ |
| 3 | E3 | NMR: 1.89 (2H, m), 2.20 (2H, m), 3.18 (1H, m), 3.37 (1H, m), 3.47 (1H, m), 4.05 (1H, m), 4.19 (1H, m), 7.42 (3H, m), 7.66 (1H, m), 8.07 (2H, m), 8.44 (2H, m); ESI+: 369.2 [M + H]+ |
| 4 | E4 | ESI+: 369 [M + H]+ |
| 5 | E5 | ESI+: 351.2 [M + H]+ |
| 6 | E6 | ESI+: 350 [M + H]+ |
| 7 | E7 | ESI+: 364 [M + H]+ |
| 8 | E8 | ESI+: 368 [M + H]+ |
| 9 | E9 | NMR: 2.19 (2H, m), 2.39 (2H, m), 3.38 (2H, m), 4.18 (2H, m), 5.24 (1H, m), 7.47 (1H, dd, J = 4.8, 9.3 Hz), 7.53-7.61 (3H, m), 7.68 (1H, m), 8.07-8.10 (2H, m), 8.45 (1H, dd, J = 1.3, 4.8 Hz), 8.47 (1H, d, J = 3.7 Hz); ESI+: 351 [M + H]+ |
| 10 | E10 | ESI+: 398 [M + H]+ |
| 11 | E1 | FAB+: 400.1 [M + H]+ |
| 12 | E1 | ESI+: 400.1 [M + H]+ |
| 13 | E1 | ESI+: 400.0 [M + H]+ |
| 14 | E1 | NMR: 1.80 (2H, m), 2.01 (2H, m), 3.04 (2H, m), 3.25 (1H, m), 4.07 (1H, m), 4.22 (1H, m), 7.15 (0.8H, m), 7.22 (0.2H, m), 7.32 (1.8H, m), 7.39 (0.2H, m), 7.46 (1H, m), 7.52 (0.8H, m), 7.65 (1.4H, m), 7.75 (1.8H, m), 8.44 (2H, m), 11.87 (0.8H, s), 12.05 (0.2H, s); ESI+: 348.40 [M + H]+ |
| 15 | E1 | NMR: 1.82 (2H, m), 2.08 (2H, m), 3.13 (2H, m), 3.31 (1H, m), 4.08 (1H, m), 4.22 (1H, m), 7.45 (4H, m), 7.65 (1H, m), 7.99 (2H, d, J = 7.0 Hz), 8.44 (2H, m), 13.83 (1H, brs); ESI+: 349.39 [M + H]+ |
| 16 | E1 | FAB+: 365 [M + H]+ |
| 17 | E1 | FAB+: 365 [M + H]+ |
| 18 | E1 | FAB+: 365 [M + H]+ |
| 19 | E1 | ESI+: 365 [M + H]+ |
| 20 | E1 | ESI+: 363 [M + H]+ |

TABLE 33

| Ex | Syn | Data |
|---|---|---|
| 21 | E1 | ESI+: 364 [M + H]+ |
| 22 | E1 | ESI+: 379 [M + H]+ |
| 23 | E1 | ESI+: 379 [M + H]+ |
| 24 | E1 | ESI+: 383 [M + H]+ |
| 25 | E1 | ESI+: 383 [M + H]+ |
| 26 | E1 | ESI+: 397 [M + H]+ |
| 27 | E1 | ESI+: 383 [M + H]+ |
| 28 | E1 | ESI+: 383 [M + H]+ |
| 29 | E1 | ESI+: 397 [M + H]+ |
| 30 | E1 | ESI+: 368 [M + H]+ |
| 31 | E1 | NMR: 1.80 (2H, m), 2.26 (2H, m), 2.47 (3H, s), 3.06-3.34 (3H, m), 4.14 (2H, m), 7.24-7.36 (3H, m), 7.52 (1H, dd, J = 2.7, 8.4 Hz), 8.03 (1H, m), 8.28 (2H, d, J = 2.7 Hz), 13.82 (1H, br s); ESI+: 382 [M + H]+ |
| 32 | E1 | ESI+: 396 [M + H]+ |
| 33 | E1 | ESI+: 369 [M + H]+ |
| 34 | E1 | ESI+: 383 [M + H]+ |
| 35 | E1 | ESI+: 383 [M + H]+ |
| 36 | E1 | ESI+: 397 [M + H]+ |
| 37 | E1 | ESI+: 397 [M + H]+ |
| 38 | E1 | FAB+: 382 [M + H]+ |
| 39 | E1 | ESI+: 401 [M + H]+ |
| 40 | E1 | ESI+: 415 [M + H]+ |
| 41 | E1 | ESI+: 368 [M + H]+ |
| 42 | E1 | NMR: 1.80 (2H, m), 2.12 (2H, m), 2.47 (3H, s), 3.10-3.44 (3H, m), 4.08 (2H, m), 7.28-7.35 (3H, m), 7.53 (1H, dd, J = 2.8, 8.4 Hz), 7.57 (1H, s), 7.73-7.78 (2H, m), 7.29 (1H, d, J = 2.8 Hz); ESI+: 382 [M + H]+ |
| 43 | E1 | NMR: 1.85 (2H, m), 2.17 (2H, m), 2.67 (3H, s), 3.20-3.43 (3H, m), 4.10 (2H, m), 7.33 (2H, m), 7.60 (1H, s), 7.76 (2H, m), 7.92 (1H, dd, J = 5.7, 8.3 Hz), 8.41 (1H, dd, J = 1.0, 8.3 Hz), 8.66 (1H, dd, J = 1.0, 5.7 Hz); ESI+: 382 [M + H]+ |
| 44 | E1 | FAB+: 401 [M + H]+ |
| 45 | E1 | ESI+: 398.2 [M + H]+ |

TABLE 33-continued

| | | |
|---|---|---|
| 46 | E1 | ESI+: 398.2 [M + H]+ |
| 47 | E1 | ESI+: 398.2 [M + H]+ |
| 48 | E1 | ESI+: 382.2 [M + H]+ |

TABLE 34

| | | |
|---|---|---|
| 49 | E1 | ESI+: 382.2 [M + H]+ |
| 50 | E1 | NMR: 1.85 (2H, m), 2.13 (2H, m), 2.62 (3H, s), 3.21 (2H, m), 3.35 (1H, t, J = 11.4 Hz), 4.06 (1H, t, J = 13.0 Hz), 4.26 (1H, d, J = 13.3 Hz), 7.3-7.4 (2H, m), 7.52 (1H, m), 7.85 (1H, m), 8.00 (1H, dt, J = 1.9, 7.7 Hz), 8.33 (1H, d, J = 8.0 Hz), 8.63 (1H, dd, J = 1.4, 5.6 Hz); FAB+: 382.1 [M + H]+ |
| 51 | E1 | ESI+: 401 [M + H]+ |
| 52 | E1 | FAB+: 396.1 [M + H]+ |
| 53 | E1 | ESI+: 396.2 [M + H]+ |
| 54 | E1 | ESI+: 415 [M + H]+ |
| 55 | E1 | ESI+: 415 [M + H]+ |
| 56 | E1 | FAB+: 415 [M + H]+ |
| 57 | E1 | FAB+: 400.1 [M + H]+ |
| 58 | E1 | FAB+: 401 [M + H]+ |
| 59 | E1 | FAB+: 401 [M + H]+ |
| 60 | E1 | NMR: 1.80 (2H, m), 2.11 (2H, m), 2.30 (3H, s), 2.42 (3H, s), 3.08-3.42 (3H, m), 3.04-4.34 (2H, m), 7.11 (1H, d, J = 8.3 Hz), 7.41 (1H, d, J = 8.3 Hz), 7.68-7.78 (1H, m), 7.96-8.04 (1H, m), 8.12-8.21 (1H, m); FAB+: 415 [M + H]+ |
| 61 | E1 | FAB+: 415 [M + H]+ |
| 62 | E1 | FAB+: 400.1 [M + H]+ |
| 63 | E1 | FAB+: 414.1 [M + H]+ |
| 64 | E1 | ESI+: 401 [M + H]+ |
| 65 | E1 | ESI+: 401 [M + H]+ |
| 66 | E1 | ESI+: 415 [M + H]+ |
| 67 | E1 | ESI+: 415 [M + H]+ |
| 68 | E1 | ESI+: 348.3 [M + H]+ |
| 69 | E1 | NMR: 2.00 (2H, m), 2.11 (2H, m), 2.47 (3H, s), 3.05 (1H, m), 3.21 (1H, m), 4.16 (1H, d, J = 12.4 Hz), 4.37 (2H, m), 7.21 (1H, m), 7.31 (1H, d, J = 8.4 Hz), 7.37 (2H, t, J = 7.9 Hz), 7.53 (1H, dd, J = 2.9, 8.4 Hz), 7.76 (2H, m), 7.90 (1H, d, J = 1.0 Hz), 7.96 (1H, s), 8.30 (1H, d, J = 2.8 Hz); ESI+: 363.3 [M + H]+ |
| 70 | E1 | ESI+: 363.3 [M + H]+ |
| 71 | E1 | ESI+: 377.3 [M + H]+ |

TABLE 35

| | | |
|---|---|---|
| 72 | E1 | NMR: 1.89-2.20 (4H, m), 2.47 (3H, s), 3.02-3.35 (2H, m), 4.03-4.38 (2H, m), 4.45-4.57 (1H, m), 6.73 (1H, d, J = 2.3 Hz), 7.23-7.33 (2H, m), 7.35-7.43 (2H, m), 7.53 (1H, dd, J = 2.8, 8.4 Hz), 7.75-7.83 (2H, m), 7.89 (1H, d, J = 2.3 Hz), 8.30 (1H, d, J = 2.8 Hz); ESI+: 363 [M + H]+ |
| 73 | E1 | NMR: 1.87-2.22 (4H, m), 3.05-3.35 (2H, m), 4.03-4.36 (2H, m), 4.40-4.54 (1H, m), 7.13-7.25 (2H, m), 7.47 (1H, dd, J = 4.3, 8.3 Hz), 7.56-7.69 (3H, m), 7.90 (1H, m), 8.29 (1H, brs), 8.43-8.47 (2H, m); FAB+: 367 [M + H]+ |
| 74 | E1 | ESI+: 381 [M + H]+ |
| 75 | E1 | ESI+: 381 [M + H]+ |
| 76 | E1 | NMR: 1.88-2.27 (4H, m), 2.47 (3H, s), 3.05-3.35 (2H, m), 4.06-4.40 (2H, m), 4.56-4.70 (1H, m), 7.25-7.34 (3H, m), 7.53 (1H, dd, J = 2.8, 8.4 Hz), 8.00-8.07 (2H, m), 8.30 (1H, d, J = 2.8 Hz), 8.68 (1H, s); ESI+: 382 [M + H]+ |
| 77 | E1 | ESI+: 368 [M + H]+ |
| 78 | E1 | ESI+: 349.2 [M + H]+ |
| 79 | E1 | NMR: 2.10 (2H, m), 2.25 (2H, m), 3.23 (1H, m), 3.36 (1H, m), 4.06 (1H, m), 4.22 (1H, m), 4.88 (1H, m), 7.32 (2H, m), 7.46 (1H, dd, J = 4.9, 8.2 Hz), 7.67 (2H, m), 7.90 (1H, s), 8.45 (2H, m); ESI+: 367.38 [M + H]+ |
| 80 | E1 | ESI+: 382.2 [M + H]+ |
| 81 | E1 | ESI+: 382.2 [M + H]+ |
| 82 | E1 | ESI+: 363.2 [M + H]+ |
| 83 | E1 | ESI+: 363.2 [M + H]+ |
| 84 | E1 | ESI+: 350.2 [M + H]+ |
| 85 | E3 | ESI+: 419 [M + H]+ |
| 86 | E3 | ESI+: 419 [M + H]+ |
| 87 | E3 | ESI+: 385 [M + H]+ |
| 88 | E3 | ESI+: 385 [M + H]+ |
| 89 | E3 | ESI+: 419 [M + H]+ |
| 90 | E3 | ESI+: 369 [M + H]+ |

TABLE 35-continued

| | | |
|---|---|---|
| 91 | E3 | ESI+: 369 [M + H]+ |
| 92 | E4 | ESI+: 369.2 [M + H]+ |
| 93 | E4 | ESI+: 385.2 [M + H]+ |
| 94 | E4 | ESI+: 385.2 [M + H]+ |
| 95 | E4 | ESI+: 385.2 [M + H]+ |

TABLE 36

| | | |
|---|---|---|
| 96 | E4 | ESI+: 369.2 [M + H]+ |
| 97 | E4 | NMR: 1.78-2.03 (2H, m), 2.15-2.25 (2H, m), 2.29 (3H, s), 3.13-3.50 (3H, m), 3.95-4.30 (2H, m), 7.11 (2H, d, J = 8.0 Hz), 7.48 (2H, d, J = 8.1 Hz), 7.69 (1H, dd, J = 8.4, 5.0 Hz), 7.94-8.00 (3H, m), 8.23 (2H, d, J = 8.1 Hz), 8.57 (1H, dd, J = 5.2, 1.4 Hz), 8.65 (1H, d, J = 2.6 Hz); ESI+: 419.2 [M + H]+ |
| 98 | E4 | ESI+: 418 [M + H]+ |
| 99 | E4 | ESI+: 387.2 [M + H]+ |
| 100 | E4 | ESI+: 387.2 [M + H]+ |
| 101 | E4 | ESI+: 387.2 [M + H]+ |
| 102 | E4 | NMR: 1.75-2.00 (2H, m), 2.10-2.25 (2H, m), 2.29 (3H, s), 3.15-3.50 (3H, m), 3.95-4.17 (2H, m), 7.11 (2H, d, J = 7.9 Hz), 7.48 (2H, d, J = 8.1 Hz), 7.67-7.76 (2H, m), 7.88-7.92 (1H, m), 8.02-8.10 (2H, m), 8.60-8.61 (1H, m), 8.71 (1H, d, J = 2.4 Hz); ESI+: 387.2 [M + H]+ |
| 103 | E4 | ESI+: 401 [M + H]+ |
| 104 | E6 | ESI+: 368 [M + H]+ |
| 105 | E6 | ESI+: 368 [M + H]+ |
| 106 | E6 | ESI+: 368 [M + H]+ |
| 107 | E6 | ESI+: 384, 386 [M + H]+ |
| 108 | E6 | NMR: 2.07 (2H, m), 2.25 (2H, m), 3.26 (2H, m), 4.22 (2H, m), 4.90 (1H, m), 7.40 (1H, m), 7.46-7.52 (2H, m), 7.67 (1H, m), 7.83 (1H, m), 7.91 (1H, m), 8.45-8.47 (2H, m), 8.85 (1H, s); ESI+: 384, 386 [M + H]+ |
| 109 | E6 | ESI+: 384, 386 [M + H]+ |
| 110 | E6 | ESI+: 386 [M + H]+ |
| 111 | E6 | ESI+: 386 [M + H]+ |
| 112 | E6 | ESI+: 382 [M + H]+ |
| 113 | E6 | ESI+: 382 [M + H]+ |
| 114 | E6 | ESI+: 382 [M + H]+ |
| 115 | E6 | ESI+: 398 [M + H]+ |
| 116 | E6 | ESI+: 398 [M + H]+ |
| 117 | E6 | ESI+: 398 [M + H]+ |
| 118 | E6 | FAB+: 432 [M + H]+ |
| 119 | E6 | ESI+: 432 [M + H]+ |
| 120 | E6 | ESI+: 400 [M + H]+ |
| 121 | E6 | ESI+: 400 [M + H]+ |
| 122 | E6 | ESI+: 400 [M + H]+ |

TABLE 37

| | | |
|---|---|---|
| 123 | E6 | FAB+: 382 [M + H]+ |
| 124 | E6 | FAB+: 382 [M + H]+ |
| 125 | E6 | FAB+: 382 [M + H]+ |
| 126 | E6 | ESI+: 398 [M + H]+ |
| 127 | E6 | FAB+: 398 [M + H]+ |
| 128 | E6 | FAB+: 398 [M + H]+ |
| 129 | E6 | ESI+: 432 [M + H]+ |
| 130 | E6 | FAB+: 432 [M + H]+ |
| 131 | E6 | ESI+: 432 [M + H]+ |
| 132 | E6 | FAB+: 400 [M + H]+ |
| 133 | E6 | FAB+: 400 [M + H]+ |
| 134 | E6 | ESI+: 400 [M + H]+ |
| 135 | E7 | ESI+: 382 [M + H]+ |
| 136 | E7 | NMR: 1.77 (2H, m), 2.12 (2H, m), 2.46 (3H, s), 3.10-3.35 (3H, m), 4.09 (2H, m), 7.28 (1H, d, J = 8.6 Hz), 7.48-7.53 (3H, m), 7.79 (2H, m), 8.27 (1H, d, J = 2.8 Hz), 8.60 (1H, s); ESI+: 398 [M + H]+ |
| 137 | E7 | ESI+: 382 [M + H]+ |
| 138 | E7 | ESI+: 364 [M + H]+ |
| 139 | E7 | ESI+: 382 [M + H]+ |
| 140 | E7 | NMR: 1.79 (2H, m), 2.12 (2H, m), 2.46 (3H, s), 3.10-3.30 (3H, m), 4.00-4.19 (2H, m), 7.24-7.29 (3H, m), 7.51 (1H, dd, J = 2.7, 8.5 Hz), 7.81 (2H, m), 8.28 (1H, d, J = 2.7 Hz), 8.53 (1H, s); ESI+: 382 [M + H]+ |
| 141 | E7 | ESI+: 400 [M + H]+ |
| 142 | E8 | ESI+: 350 [M + H]+ |
| 143 | E8 | ESI+: 382 [M + H]+ |
| 144 | E8 | NMR: 1.84 (2H, m), 2.17 (2H, m), 2.58 (3H, s), 3.18-3.30 (2H, m), 3.38 (1H, m), 4.01 (1H, m), 4.21 (1H, m), 7.20 (1H, m), 7.58 (3H, m), |

TABLE 37-continued

|     |     | 7.71 (1H, s), 7.76 (1H, dd, J = 5.4, 8.4 Hz), 8.21 (1H, d, J = 8.1 Hz), 8.59 (1H, dd, J = 1.4, 5.4 Hz); ESI+: 382 [M + H]+ |
|-----|-----|---|
| 145 | E8  | ESI+: 382 [M + H]+ |
| 146 | E8  | ESI+: 382 [M + H]+ |
| 147 | E8  | ESI+: 368 [M + H]+ |
| 148 | E10 | ESI+: 431.9 [M + H]+ |
| 149 | E10 | ESI+: 399.9 [M + H]+ |
| 150 | E10 | ESI+: 431.9 [M + H]+ |

TABLE 38

| 151 | E10 | ESI+: 398 [M + H]+ |
| 152 | E10 | ESI+: 400 [M + H]+ |
| 153 | E10 | ESI+: 400 [M + H]+ |
| 154 | E10 | ESI+: 400 [M + H]+ |
| 155 | E10 | ESI+: 400 [M + H]+ |
| 156 | E10 | ESI+: 432 [M + H]+ |
| 157 | E10 | ESI+: 432 [M + H]+ |
| 158 | E10 | ESI+: 399.9 [M + H]+ |
| 159 | E3  | ESI+: 351.2 [M + H]+ |

Industrial Applicability

The compound of the formula (I) or a pharmaceutically acceptable salt thereof has an FAAH inhibitory activity, and can be used as an agent for preventing and/or treating FAAH-related diseases, in particular, neuropathic pain.

The invention claimed is:

1. A compound of the formula (I) or a pharmaceutically acceptable salt thereof:

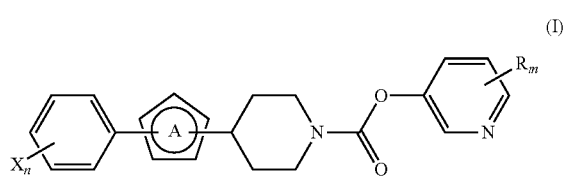

wherein
Ring A represents an azole ring,
R is the same as or different from each other, and represents H or lower alkyl,
X is the same as or different from each other, and represents H, halogen, or halogeno-lower alkyl,
n and m are the same as or different from each other and represent 1 or 2.

2. The compound as described in claim 1, which is selected from the group consisting of:
pyridin-3-yl 4-(3-phenyl-1H-1,2,4-triazol-5-yl)piperidine-1-carboxylate,
6-methylpyridin-3-yl 4-[3-(4-fluorophenyl)-1H-1,2,4-triazol-5-yl]piperidine-1-carboxylate,
6-methylpyridin-3-yl 4-[5-(4-fluorophenyl)-1,3-oxazol-2-yl]piperidine-1-carboxylate,
2,6-dimethylpyridin-3-yl 4-[5-(3,4-difluorophenyl)-1,2,4-oxadiazol-3-yl]piperidine-1-carboxylate,
2-methylpyridin-3-yl 4-[3-(2-fluorophenyl)-1H-1,2,4-triazol-5-yl]piperidine-1-carboxylate,
6-methylpyridin-3-yl 4-(3-phenyl-1H-pyrazol-1-yl)piperidine-1-carboxylate,
2-methylpyridin-3-yl 4-[5-(3-fluorophenyl)-1,3-oxazol-2-yl]piperidine-1-carboxylate, and
6-methylpyridin-3-yl 4-[4-(4-fluorophenyl)-1,3-oxazol-2-yl]piperidine-1-carboxylate,
or a pharmaceutically acceptable salt thereof.

3. A pharmaceutical composition comprising the compound as described in claim 1 or a pharmaceutically acceptable salt thereof, and a pharmaceutically acceptable excipient.

4. The compound as described in claim 2, which is pyridin-3-yl 4-(3-phenyl-1H-1,2,4-triazol-5-yl)piperidine-1-carboxylate or a pharmaceutically acceptable salt thereof.

5. The compound as described in claim 2, which is 6-methylpyridin-3-yl 4-[3-(4-fluorophenyl)-1H-1,2,4-triazol-5-yl]piperidine-1-carboxylate or a pharmaceutically acceptable salt thereof.

6. The compound as described in claim 2, which is 6-methylpyridin-3-yl 4-[5-(4-fluorophenyl)-1,3-oxazol-2-yl]piperidine-1-carboxylate or a pharmaceutically acceptable salt thereof.

7. The compound as described in claim 2, which is 2,6-dimethylpyridin-3-yl 4-[5-(3,4-difluorophenyl)-1,2,4-oxadiazol-3-yl]piperidine-1-carboxylate or a pharmaceutically acceptable salt thereof.

8. The compound as described in claim 2, which is 2-methylpyridin-3-yl 4-[3-(2-fluorophenyl)-1H-1,2,4-triazol-5-yl]piperidine-1-carboxylate or a pharmaceutically acceptable salt thereof.

9. The compound as described in claim 2, which is 6-methylpyridin-3-yl 4-(3-phenyl-1H-pyrazol-1-yl)piperidine-1-carboxylate or a pharmaceutically acceptable salt thereof.

10. The compound as described in claim 2, which is 2-methylpyridin-3-yl 4-[5-(3-fluorophenyl)-1,3-oxazol-2-yl]piperidine-1-carboxylate or a pharmaceutically acceptable salt thereof.

11. The compound as described in claim 2, which is 6-methylpyridin-3-yl 4-[4-(4-fluorophenyl)-1,3-oxazol-2-yl]piperidine-1-carboxylate or a pharmaceutically acceptable salt thereof.

12. A method for treating neuropathic pain, comprising administering to a patient in need thereof an effective amount of the compound as described in claim 1 or a pharmaceutically acceptable salt thereof.

* * * * *